US009495952B2

(12) United States Patent
Park et al.

(10) Patent No.: US 9,495,952 B2
(45) Date of Patent: Nov. 15, 2016

(54) ELECTRONIC DEVICES FOR CONTROLLING NOISE

(75) Inventors: Hyun Jin Park, San Diego, CA (US); Brian Lee Momeyer, San Diego, CA (US); Jeremy Patrick Toman, San Diego, CA (US); Kwokleung Chan, San Diego, CA (US); Hui-ya Liao Nelson, San Diego, CA (US); Louis Dominic Oliveira, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 936 days.

(21) Appl. No.: 13/569,031

(22) Filed: Aug. 7, 2012

(65) Prior Publication Data

US 2013/0039507 A1 Feb. 14, 2013

Related U.S. Application Data

(60) Provisional application No. 61/521,177, filed on Aug. 8, 2011.

(51) Int. Cl.
*A61F 11/06* (2006.01)
*G10K 11/16* (2006.01)
(Continued)

(52) U.S. Cl.
CPC ......... *G10K 11/1788* (2013.01); *G10K 11/178* (2013.01); *G10K 2210/1053* (2013.01);
(Continued)

(58) Field of Classification Search
CPC .................. G10K 2210/1081; G10K 11/178; G10K 11/1788; G10K 2210/3055; G10K 2210/1053; G10K 2210/129; G10K 2210/321; G10K 2210/501; G10K 2210/504
USPC ............................................... 381/71.1, 71.6
See application file for complete search history.

(56) References Cited

U.S. PATENT DOCUMENTS 5,267,320 A 11/1993 Fukumizu
5,937,070 A 8/1999 Todter et al.
(Continued)

FOREIGN PATENT DOCUMENTS

CN 101385385 A 3/2009
EP 0715131 A2 6/1996
(Continued)

OTHER PUBLICATIONS

International Search Report and Written Opinion—PCT/US2012/050010—ISA/EPO—Jul. 29, 2013.
(Continued)

*Primary Examiner* — Paul S Kim
(74) *Attorney, Agent, or Firm* — Austin Rapp & Hardman

(57) ABSTRACT

An electronic device for controlling noise is described. The electronic device includes a force sensor for detecting a force on the electronic device. The electronic device also includes noise control circuitry for generating a noise control signal based on a noise signal and the force. Another electronic device for controlling noise is also described. The electronic device includes a speaker that outputs a runtime ultrasound signal, an error microphone that receives a runtime ultrasound channel signal and noise control circuitry coupled to the speaker and to the error microphone. The noise control circuitry determines at least one calibration parameter and determines a runtime channel response based on the runtime ultrasound channel signal. The noise control circuitry also determines a runtime placement based on the runtime channel response and the at least one calibration parameter and determines at least one runtime active noise control parameter based on the runtime placement.

42 Claims, 19 Drawing Sheets

(51) Int. Cl.
*H03B 29/00* (2006.01)
*G10K 11/178* (2006.01)

(52) U.S. Cl.
CPC . *G10K2210/1081* (2013.01); *G10K 2210/129* (2013.01); *G10K 2210/3055* (2013.01); *G10K 2210/321* (2013.01); *G10K 2210/501* (2013.01); *G10K 2210/504* (2013.01)

(56) References Cited

U.S. PATENT DOCUMENTS

| | | | | |
|---|---|---|---|---|
| 6,118,878 | A * | 9/2000 | Jones | G10K 11/178 381/71.11 |
| 6,449,369 | B1 | 9/2002 | Carme et al. | |
| 6,503,197 | B1 | 1/2003 | Nemirovski | |
| 6,704,428 | B1 | 3/2004 | Wurtz | |
| 6,748,087 | B1 | 6/2004 | Jones | |
| 2009/0034748 | A1 | 2/2009 | Sibbald | |
| 2010/0045612 | A1 | 2/2010 | Molne | |
| 2010/0246855 | A1 | 9/2010 | Chen | |
| 2011/0002474 | A1 | 1/2011 | Fuller | |
| 2011/0002476 | A1 * | 1/2011 | Morishima | G10K 11/178 381/71.6 |
| 2012/0057718 | A1 | 3/2012 | Vernon | |

FOREIGN PATENT DOCUMENTS

| | | | |
|---|---|---|---|
| EP | 0967592 | A2 | 12/1999 |
| GB | 2234881 | A | 2/1991 |
| JP | 2005292250 | A | 10/2005 |
| JP | 2009262887 | A | 11/2009 |
| JP | 2010239508 | A | 10/2010 |
| JP | 2011013403 | A | 1/2011 |
| KR | 100212780 | B1 | 8/1999 |
| WO | 2010117714 | A1 | 10/2010 |

OTHER PUBLICATIONS

Partial International Search Report—PCT/US2012/050010—ISA/EPO—Apr. 17, 2013.

* cited by examiner

ELECTRONIC DEVICES FOR CONTROLLING NOISE

RELATED APPLICATIONS

This application is related to and claims priority from U.S. Provisional Patent Application Ser. No. 61/521,177 filed Aug. 8, 2011, for "CONTROLLING NOISE USING FORCE ON AN ELECTRONIC DEVICE."

TECHNICAL FIELD

The present disclosure relates generally to electronic devices. More specifically, the present disclosure relates to electronic devices for controlling noise.

BACKGROUND

In the last several decades, the use of electronic devices has become common. In particular, advances in electronic technology have reduced the cost of increasingly complex and useful electronic devices. Cost reduction and consumer demand have proliferated the use of electronic devices such that they are practically ubiquitous in modern society. As the use of electronic devices has expanded, so has the demand for new and improved features of electronic devices. More specifically, electronic devices that perform functions faster, more efficiently or with higher quality are often sought after.

Some electronic devices (e.g., cellular phones, smartphones, headphones, music players, etc.) may be used in noisy environments. For example, a cellular phone may be used in an airport where environmental, background or ambient noise may be distracting to a user. For instance, a user may be engaged in a phone call while others are talking nearby or while an airplane is taking off. These environmental noises may make it difficult for an electronic device user to hear acoustic signals (e.g., speech, music, etc.) output from the electronic device.

As can be observed from the foregoing discussion, environmental, background or ambient noise may degrade acoustic signals output from an electronic device. Accordingly, systems and methods that may help to control noise may be beneficial.

SUMMARY

An electronic device for controlling noise is disclosed. The electronic device may include a force sensor for detecting a force on the electronic device. The electronic device may also include noise control circuitry for generating a noise control signal based on a noise signal and the force. Generating the noise control signal may not involve an iterative convergence process but may involve a direct calculation. The electronic device may not use an error microphone signal for generating the noise control signal. The electronic device may be a wireless communication device.

The electronic device may also include a microphone for capturing the noise signal. The electronic device may additionally include a speaker for outputting the noise control signal.

Generating the noise control signal may include adapting an adaptive filter based on the force. Adapting the adaptive filter may be based on a correlation between a transfer function and the force. Adapting the adaptive filter may include determining a first scaling factor and a second scaling factor based on the force. Adapting the adaptive filter may further include multiplying a first base transfer function by the first scaling factor to produce a first product. Adapting the adaptive filter may additionally include multiplying a second base transfer function by the second scaling factor to produce a second product. Adapting the adaptive filter may also include multiplying a negative of the first product by a reciprocal of the second product to produce filter coefficients. Adapting the adaptive filter may further include controlling the adaptive filter using the filter coefficients to generate the noise control signal.

Adapting the adaptive filter may be performed according to an equation $$W(z) = \frac{-g(R)P_o(z)}{[h(R)S_o(z)]}.$$

$P_o(z)$ may be a first transfer function at a first force. g may be a first scaling function of a force value R. z may be a complex number. $S_o(z)$ may be a second transfer function at a second force. h may be a second scaling function of the force value R. W(z) may represent the adaptive filter.

The force sensor may continually measure the force and provide a force signal based on the force. The adaptive filter may be continually adapted based on the force signal.

The electronic device may include a plurality of force sensors for detecting the force on the electronic device. The plurality of force sensors may be positioned proximate corners of the electronic device. The plurality of force sensors may be positioned proximate a speaker on the electronic device. The force sensor may be positioned behind a speaker on the electronic device. The force sensor may be a gasket-type force sensor. The force may be a force between the electronic device and a user's ear or face.

A method for controlling noise by an electronic device is also disclosed. The method includes detecting a force on an electronic device. The method also includes generating a noise control signal based on a noise signal and the force.

A computer-program product for controlling noise is also disclosed. The computer-program product includes a non-transitory tangible computer-readable medium with instructions. The instructions include code for causing an electronic device to detect a force on the electronic device. The instructions further include code for causing the electronic device to generate a noise control signal based on a noise signal and the force.

An apparatus for controlling noise is also disclosed. The apparatus includes means for detecting a force on an electronic device. The apparatus also includes means for generating a noise control signal based on a noise signal and the force.

Another electronic device for controlling noise is also described. The electronic device includes a speaker that outputs a runtime ultrasound signal. The electronic device also includes an error microphone that receives a runtime ultrasound channel signal. The electronic device further includes noise control circuitry coupled to the speaker and to the error microphone. The noise control circuitry determines at least one calibration parameter, determines at least one runtime channel response parameter based on the runtime ultrasound channel signal, determines a runtime placement based on the at least one runtime channel response parameter and the at least one calibration parameter and determines at least one runtime active noise control parameter based on the runtime placement.

The electronic device may include a noise microphone that receives a noise signal. The noise control circuitry may generate a noise control signal based on the noise signal and the at least one runtime active noise control parameter.

Determining the at least one calibration parameter may include determining at least one calibration active noise control parameter and outputting a calibration ultrasound signal. Determining the at least one calibration parameter may also include receiving a calibration ultrasound channel signal and determining at least one calibration channel response parameter based on the calibration ultrasound channel signal.

The at least one calibration parameter may include at least one calibration active noise control parameter and/or at least one calibration channel response parameter. Determining the runtime placement may include selecting a calibration placement with at least one calibration channel response parameter that is nearest to the at least one runtime channel response parameter.

Determining at least one runtime active noise control parameter may include selecting at least one calibration active noise control parameter. Determining at least one runtime active noise control parameter may include interpolating calibration active noise control parameters.

Another method for controlling noise by an electronic device is also described. The method includes determining at least one calibration parameter. The method also includes outputting a runtime ultrasound signal. The method further includes receiving a runtime ultrasound channel signal. The method additionally includes determining at least one runtime channel response parameter based on the runtime ultrasound channel signal. The method also includes determining a runtime placement based on the at least one runtime channel response parameter and the at least one calibration parameter. The method further includes determining at least one runtime active noise control parameter based on the runtime placement.

Another computer-program product for controlling noise is also described. The computer-program product includes a non-transitory tangible computer-readable medium with instructions. The instructions include code for causing an electronic device to determine at least one calibration parameter. The instructions also include code for causing the electronic device to output a runtime ultrasound signal. The instructions further include code for causing the electronic device to receive a runtime ultrasound channel signal. The instructions additionally include code for causing the electronic device to determine at least one runtime channel response parameter based on the runtime ultrasound channel signal. The instructions also include code for causing the electronic device to determine a runtime placement based on the at least one runtime channel response parameter and the at least one calibration parameter. The instructions further include code for causing the electronic device to determine at least one runtime active noise control parameter based on the runtime placement.

Another apparatus for controlling noise is also described. The apparatus includes means for determining at least one calibration parameter. The apparatus also includes means for outputting a runtime ultrasound signal. The apparatus further includes means for receiving a runtime ultrasound channel signal. The apparatus additionally includes means for determining at least one runtime channel response parameter based on the runtime ultrasound channel signal. The apparatus also includes means for determining a runtime placement based on the at least one runtime channel response parameter and the at least one calibration parameter. The apparatus further includes means for determining at least one runtime active noise control parameter based on the runtime placement.

DETAILED DESCRIPTION

Figure 1:
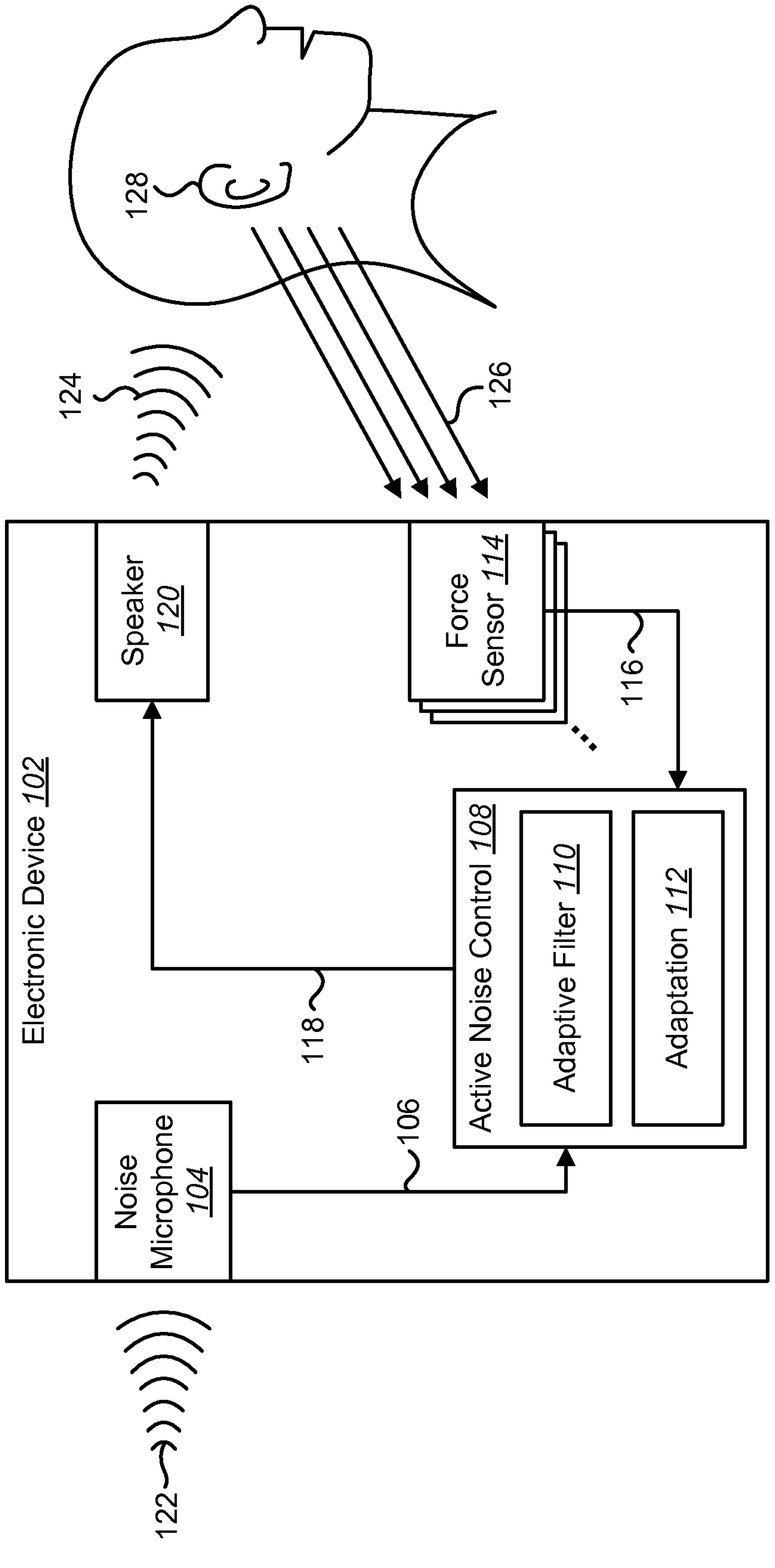
FIG. 1 is a block diagram illustrating one configuration of an electronic device in which systems and methods for controlling noise using force may be implemented.

The systems and methods disclosed herein may be applied to a variety of electronic devices. Examples of electronic devices include cellular phones, smartphones, headphones, video cameras, audio players (e.g., Moving Picture Experts Group-1 (MPEG-1) or MPEG-2 Audio Layer 3 (MP3) players), video players, audio recorders, desktop computers/laptop computers, personal digital assistants (PDAs), gaming systems, etc. One kind of electronic device is a communication device, which may communicate with another device. Examples of communication devices include telephones, laptop computers, desktop computers, cellular phones, smartphones, e-readers, tablet devices, gaming systems, etc.

An electronic device or communication device may operate in accordance with certain industry standards, such as International Telecommunication Union (ITU) standards and/or Institute of Electrical and Electronics Engineers (IEEE) standards (e.g., Wireless Fidelity or “Wi-Fi” standards such as 802.11a, 802.11b, 802.11g, 802.11n and/or 802.11ac). Other examples of standards that a communication device may comply with include IEEE 802.16 (e.g., Worldwide Interoperability for Microwave Access or “WiMAX”), Third Generation Partnership Project (3GPP), 3GPP Long Term Evolution (LTE), Global System for Mobile Telecommunications (GSM) and others (where a communication device may be referred to as a User Equipment (UE), NodeB, evolved NodeB (eNB), mobile device, mobile station, subscriber station, remote station, access terminal, mobile terminal, terminal, user terminal, subscriber unit, etc., for example). While some of the systems and methods disclosed herein may be described in terms of one or more standards, this should not limit the scope of the disclosure, as the systems and methods may be applicable to many systems and/or standards.

It should be noted that some communication devices may communicate wirelessly and/or may communicate using a wired connection or link. For example, some communication devices may communicate with other devices using an Ethernet protocol. The systems and methods disclosed herein may be applied to communication devices that communicate wirelessly and/or that communicate using a wired connection or link.

As used herein, the terms, “cancel,” “cancellation” and other variations of the word “cancel” may or may not imply a complete cancellation of a signal. For example, if a first signal “cancels” a second signal, the first signal may interfere with the second signal in an attempt to reduce the second signal in amplitude. The resulting signal may or may not be reduced or completely cancelled.

As used herein, the terms “circuit,” “circuitry” and other variations of the term “circuit” may denote a structural element or component. For example, circuitry can be an aggregate of circuit components, such as a multiplicity of integrated circuit components, in the form of processing and/or memory cells, units, blocks and the like.

Traditionally, static or non-adaptive active noise control (ANC) consists of a filtering operation only and requires a noise signal input. Conventional, non-adaptive ANC may be applied to a handset. In one example of feed-forward ANC, a noise microphone may be placed on the back of the handset, while a speaker (e.g., earpiece, receiver, etc.) may be placed on the front of the handset, which a user may hold near his/her ear. ANC processing may use a noise signal provided by the noise microphone in an attempt to cancel noise by outputting a signal from the speaker.

Adaptive ANC consists of both a filtering operation and an adaptation operation. Typically, an adaptive algorithm for feed-forward (FF) ANC requires an error signal input, which measures the remaining noise signal at a “quiet zone.” Thus, traditional adaptive FF ANC requires two input signals. One input signal includes external noise and the other input signal includes an error signal (from an error microphone, for example). The filtering operation may require only the noise signal input. However, the adaptation operation may require both the noise signal input and the error signal input to function properly.

In one example of generic adaptive ANC processing, one microphone captures a noise signal and an error microphone captures an error signal e(n). In generic adaptive ANC processing, an adaptive algorithm minimizes the error signal e(n), which converges an adaptive filter W(z) to an optimal solution. Converging the adaptive filter may be referred to as an iterative convergence or training process. In this example, $$W(z) = \frac{-P(z)}{S(z)},$$

where P(z) is a first transfer function (e.g., primary path transfer function) and S(z) is a second transfer function (e.g., secondary path transfer function).

Another example of traditional adaptive ANC processing is called filtered-x least mean squares (FxLMS) adaptive ANC processing. This approach also uses an error microphone to capture an error signal e(n). An LMS algorithm uses the captured error signal e(n) to train or converge the adaptive filter W(z).

In one example, conventional adaptive ANC may be applied to a handset. In this example, a noise microphone may be placed on the back of the handset, while a speaker (e.g., earpiece, receiver, etc.) may be placed on the front of the handset, which a user may hold near his/her ear. An error microphone may also be placed on the front of the handset, near the speaker. ANC processing may use a noise signal provided by the noise microphone and an error signal provided by the error microphone in an attempt to cancel noise by outputting a signal from the speaker.

While it may be expensive to implement adaptive ANC, it may be useful in some applications. For example, applying ANC to a handset earpiece or speaker may be one application of ANC that can be benefitted by adaptive ANC, since the acoustic transfer function is highly dynamic and filter adaptation may be used to ensure optimal noise cancellation.

Conventional feed-forward (FF) adaptive active noise control (ANC) typically requires an error microphone (or some other input sensor) to pick up a sound signal at a “quiet zone.” This sound signal is usually called an error signal. The microphone that receives the error signal may typically be placed near a speaker (e.g., earpiece, receiver, etc.) to pick up the error signal. Placing the microphone near the speaker may add extra cost and complexity in acoustics design. It should be noted that the microphone that receives the error signal may be used in addition to another microphone used to pick up noise for reduction (e.g., cancellation).

When ANC is applied to a handset earpiece, the adaptive component of the ANC processing may be important. However, this typically requires extra costs due to the necessity of the error microphone placed near the receiver. These extra costs may include the following disadvantages: the physical design has extra complexity, circuit cost and complexity may increase, computation has extra cost and complexity and the overall power and device cost, weight, and size may also increase. For example, using an extra error microphone may require extra space to implement, as the error microphone may require a bias circuit.

The systems and methods disclosed herein describe an adaptive active noise control (ANC) scheme that uses information from one or more force sensors. The one or more force sensors may detect a pressing force between a device and a user's ear or face. This may be done instead of using a conventional error microphone signal.

In accordance with the systems and methods disclosed herein, a transfer function (e.g., S(z)) may vary with a pressing force or pressure. For example, it may be observed that a speaker transfer function S(z) (e.g., secondary path transfer function) dynamically varies corresponding to a pressing force. Variations in the speaker transfer function S(z) may be predictable from the pressing force. In one configuration of the systems and methods disclosed herein, a pressing force R may be mapped to an adaptive filter W(z). More detail regarding this configuration is given below.

In accordance with the systems and methods disclosed herein, force sensor-based adaptive ANC processing may be used. In this approach, changes in force or pressure detected by one or more force sensors may correspond to changes in the transfer functions P(z) and S(z). For example, the force or pressure detected by the one or more force sensors may represent a pressure between a user's ear pinna and an earpiece panel or plate. In this example, an adaptive algorithm may be used that is based on force sensor information R. The force sensor information R may indicate or measure a pressing force between an electronic device (e.g., handset) and a user's ear pinna and/or face. This force sensor information R may be mapped to a frequency response F(R,z). In some configurations, the frequency response F(R,z) may be composed from simpler functions.

It should be noted that the terms "force" and "pressure" may be used interchangeably herein. For example, force may be measured in newtons (N) and pressure may be measured in force per unit area (e.g., newtons per square meter). However, the systems and methods disclosed herein may be configured to function using force and/or pressure. For instance, force sensors or pressure sensors may be used to produce a force signal or a pressure signal in accordance with the systems and methods disclosed herein. Thus, although a component, signal, element, measurement or function is expressed in terms of force, pressure may be used and vice-versa.

More specifically, for example, it may be observed that a relationship exists between a pressing force and acoustical transfer functions as illustrated in Equations (1) and (2).

$$P(z)=g(R)P_o(z) \tag{1}$$

$$S(z)=*h(R)S_o(z) \tag{2}$$

In Equation (1), $P_o$ (z) is a transfer function (e.g., a first transfer function, noise transfer function or primary path transfer function) at a specific force or pressure, g is a scaling function of a force or pressure value R and z is a complex number. In Equation (2), $S_o(z)$ is a transfer function (e.g., a second transfer function, speaker transfer function or secondary path transfer function) at a specific force or pressure, h is a scaling function of the force or pressure value R and z is a complex number. Using these transfer functions, an optimal ANC filter may be determined as illustrated in Equation (3).

$$W(z)=\frac{-P(z)}{S(z)}=\frac{-g(R)P_o(z)}{[h(R)S_o(z)]}=F(R,z) \tag{3}$$

In Equation (3), W(z) is an adaptive filter and F(R,z) is a frequency response.

The systems and methods disclosed herein may be applied to many different configurations of electronic devices (e.g., handsets, headphones, etc.). For example, a handset may be configured for such a scheme where force or pressure sensitive sensors can measure the pressing force between a handset earpiece panel and the ear pinna. For instance, one or more force sensors can be used to measure the force at a given location, at multiple locations or the centroid of force on a touchscreen may be used if there is a plurality of force sensors placed beneath a touchscreen.

In one earpiece ANC application, experimental measurement shows that variations in the transfer functions P and S are closely correlated with pressure or force between an earpiece panel and ear pinna. In some simple cases, a predictable and calculable relationship may exist as illustrated in the following equations: $P(z)=g(R)*P_o(z)$ and $S(z)=h(R)*S_o(z)$. For example, when a user is in a noisy environment, the user may tend to press a speaker (on a handset, for example) more tightly to their ear and when the user is in a less noisy environment, the user may tend to press a speaker less tightly to their ear.

The systems and methods disclosed herein may be advantageous for several reasons. One advantage may be that the relationship described above is relatively simple and an optimal filter may be directly computed by the equation $$\frac{-P(z)}{S(z)}.$$

This direct computation or calculation may be done instead of iteratively converging or training the filter. This approach may save computation and power. Another advantage may be that there is no need to place a costly error microphone close to an earpiece speaker (e.g., receiver). This may avoid a physical volume increase and design compromises. Furthermore, an algorithm based on the systems and methods disclosed herein may be free from acoustical interference and feedback issues.

In one example, force sensor-based adaptive ANC may be applied to a handset. In this example, a noise microphone may be placed on the back of the handset, while a speaker (e.g., earpiece, receiver, etc.) may be placed on the front of the handset, which a user may hold near his/her ear. One or more force sensors may also be used in the handset. The force sensor(s) may be placed such that they detect a pressing force between the handset (e.g., earpiece panel) and a user's ear and/or face when the user holds the handset to his/her ear or face. In this example, ANC processing may use a noise signal provided by the noise microphone and a pressure or force signal provided by the one or more force sensors in an attempt to cancel or reduce noise by outputting a noise control signal from the speaker.

As mentioned above, one or more force sensors may be placed in a variety of locations. Several examples of where the one or more force sensors may be located on a handset are described as follows. In one example, four force sensors may be located at the corners of a front panel of a handset. In another example, four force sensors may be located around a speaker or earpiece on a handset. In another example, a single gasket-type force sensor may be located at a speaker or earpiece. In yet another example, a single force sensor may be located behind a speaker or earpiece on the handset. Many other configurations and/or combinations of the examples described may be used.

Some configurations of the systems and methods disclosed herein may utilize ultrasound for active noise control (e.g., cancellation). For example, active noise control parameter determination and/or adjustment may be based on ultrasound signals. As described above, ANC may be applied to reduce (e.g., "cancel") incoming noise by generating a noise control signal (e.g., anti-noise) based on the incoming noise. The strength of the noise control signal (e.g., anti-noise) may require a degree of precision for effective noise reduction (e.g., cancellation). Otherwise, not enough noise may be cancelled or too much anti-noise may result in noise injection.

The noise that reaches a user's ear may depend on the coupling or sealing between the electronic device (e.g., ANC device) and the user's ear. For example, noise leakage may depend on the holding force, position and/or fitting of the electronic device. Additionally, the effectiveness of a noise control signal (e.g., anti-noise) may depend on the holding force, position and/or loudspeaker-to-ear coupling.

In known approaches, ANC parameters are adjusted on-the-fly to reduce noise at an ANC error microphone. However, these known approaches require complicated learning rules for the adaptive filter. This learning may be unstable and create acoustic shock in some cases.

In accordance with the systems and methods disclosed herein, a channel response may be determined (e.g., measured) based on an ultrasound signal. For example, changes in the channel response may be measured using an ultrasound signal. An ultrasound signal may be an acoustic signal that is inaudible to humans. For example, an ultrasound signal may have a frequency of 20 kilohertz (kHz) or greater.

Examples of the systems and methods disclosed herein are given as follows. During a calibration stage or mode (e.g., offline) one or more of the following procedures may be performed. An electronic device (e.g., ANC device) may be arranged according to a particular placement. A placement may be or may depend on one or more of holding force, position, location, orientation, pressing force between the electronic device and a user or user model (e.g., head and torso simulator (HATS)) and coupling (e.g., sealing) between the electronic device and a user or user model (e.g., HATS). In one configuration, the electronic device (e.g., ANC device) may be mounted next to a user model (e.g., HATS).

The electronic device may determine active noise control (e.g., cancellation) (ANC) parameters. For example, the electronic device may tune for optimal active noise control parameters. The electronic device may output an ultrasound signal. For instance, the electronic device may play an ultrasound signal from a speaker. The electronic device may receive an ultrasound channel signal. For example, the electronic device may capture (e.g., record) and measure an ultrasound channel signal with an error microphone. The electronic device may determine (e.g., estimate) a channel response based on the ultrasound channel signal. For example, the electronic device may extract channel response statistics. These procedures may be repeated for various placements (e.g., a mounting position and/or force may be changed). For example, calibration procedures may be repeated for various levels of holding force and/or perturbed position. For each placement, for instance, the electronic device may determine active noise control parameters, output an ultrasound signal and receive an ultrasound channel signal.

During runtime (e.g., when the electronic device is in use), one or more of the following procedures may be performed. The electronic device may output an ultrasound signal. For example, the electronic device may send or play an ultrasound signal from a speaker. The electronic device may receive an ultrasound channel signal. For example, the electronic device may capture (e.g., record) and measure an ultrasound channel signal with an error microphone. The electronic device may determine (e.g., estimate, deduce) a channel response based on the ultrasound channel signal. For example, the electronic device may extract channel response statistics. The electronic device may determine (e.g., estimate, deduce) a placement (e.g., holding force, position, etc.) based on the channel response. The electronic device may determine (e.g., calculate, deduce, retrieve) active noise control parameters (e.g., optimal ANC parameters). For example, the electronic device may determine active noise control parameters based on the channel response.

Some configurations of the systems and methods disclosed herein may provide one or more advantages or benefits. Examples of these one or more advantages or benefits are given as follows. Ultrasound signals are inaudible to humans. Thus, ultrasound signals may be utilized to enable on-the-fly active noise control parameter adjustment (without disrupting a user, for example). In some configurations, force measurement is not required. Accordingly, no extra components may be needed (assuming adaptive active noise control, for instance), as compared to other configurations where the force is measured (as described above, for example). It should be noted, however, force measurement may be combined with ultrasound channel measurement in some configurations.

In accordance with the systems and methods disclosed herein, ultrasound channel measurement may facilitate active noise control learning. For example, adaptive active noise control may adjust for changes in noise leakage and/or changes in speaker-to-ear coupling. In particular, ultrasound channel measurement may help adjust for changes in speaker-to-ear coupling, while adaptive active noise control may focus on adjusting for changes in noise leakage. It should be noted that ultrasound channel measurement may also help adjust for changes in noise leakage, particularly if adaptive active noise control is not available. In some configurations, active noise control may be activated/deactivated based on ultrasound channel measurement.

Various configurations are now described with reference to the Figures, where like reference numbers may indicate functionally similar elements. The systems and methods as generally described and illustrated in the Figures herein could be arranged and designed in a wide variety of different configurations. Thus, the following more detailed description of several configurations, as represented in the Figures, is not intended to limit scope, as claimed, but is merely representative of the systems and methods.

FIG. 1 is a block diagram illustrating one configuration of an electronic device 102 in which systems and methods for controlling noise using force may be implemented. The electronic device 102 may include a noise microphone 104, a speaker 120, an active noise control (ANC) block/module 108 and/or one or more force sensors 114. As used herein, the term "block/module" may be used to indicate that a particular component or element may be implemented in hardware, software or a combination of both. For example, the active noise control block/module 108 may be implemented in hardware, software or a combination of both. For instance, the active noise control block/module 108 may be noise control circuitry.

The noise microphone 104 may be a transducer that converts acoustic signals 122 into electrical or electronic signals 106. For example, the noise microphone 104 may convert acoustic noise signals 122 (e.g., environmental noise, background noise, ambient noise, etc.) into an electrical or electronic noise signal 106. It should be noted that one or more noise microphones 104 may be used. The one or more noise microphones 104 may be placed in a variety of locations on the electronic device 102. For example, one or more noise microphones 104 may be placed on the back of a handset/headset, on one or more sides of a handset/headset, etc. The noise signal 106 may be provided to the active noise control block/module 108.

As mentioned above, the electronic device 102 may include one or more force sensors 114. Some examples of force sensors 114 include capacitive force sensors, piezoelectric force sensors, piezoresistive strain gauges, electromagnetic force sensors, optical force sensors, potentiometric force sensors, frame force sensors, etc. The one or more force sensors 114 may be used to detect a force 126 on the electronic device 102. For example, a user may press his/her ear 128 and/or face onto the electronic device 102. The one or more force sensors 114 may detect the force (e.g., pressure) 126 between the user's ear 128 (and/or face) and the electronic device 102. For instance, the one or more force sensors 114 may generate a force signal 116 based on the force 126 placed on the electronic device 102. The force signal 116 may indicate or reflect the force 126 detected by the force sensor(s) 114. For instance, the force signal 116 may indicate a force or pressure measurement in newtons (N). This force signal 116 may be provided to the active noise control block/module 108.

The active noise control block/module 108 may use the noise signal 106 and the force signal 116 to generate a noise control signal 118. For example, the noise control signal 118 may be used to reduce or cancel the acoustic noise 122. For instance, the noise control signal 118 may be provided to a speaker 120 that converts the noise control signal 118 into an acoustic noise control signal 124. In some configurations, the speaker 120 may exclusively output the acoustic noise control signal 124. In other configurations, the speaker 120 may output the acoustic noise control signal 124 in addition to one or more other acoustic signals (e.g., music, speech, etc.). For example, the speaker 120 may be an earpiece speaker on a cellular phone. It should be noted that one or more speakers 120 may be used.

The acoustic noise control signal 124 may have an amplitude that is similar to the acoustic noise signal 122 and may be approximately out-of-phase with the acoustic noise signal 122. In this way, the acoustic noise control signal 124 may interfere with the acoustic noise signal 122, thereby reducing or cancelling the acoustic noise signal 122. Thus, the acoustic noise signal 122 may be reduced and/or effectively eliminated as perceived by a user of the electronic device 102.

In one configuration, the active noise control block/module 108 may include an adaptive filter 110 and an adaptation block/module 112. The adaptation block/module 112 may use the force signal 116 to modify or adapt the functioning of the adaptive filter 110. For example, the adaptation block/module 112 may change the frequency response, taps or coefficients of the adaptive filter 110 based on the force signal 116. For instance, one or more transfer functions may model the transmission of the acoustic noise signal 122 and the acoustic noise control signal 124. The one or more transfer functions may be adjusted based on the force signal 116 in order to adapt the adaptive filter 110. The adaptive filter 110 may filter the noise signal 106 to produce the noise control signal 118. For example, the adaptive filter 110 may filter the noise signal 106 as determined by the adaptation block/module 112 based on the force signal 116.

Figure 2:
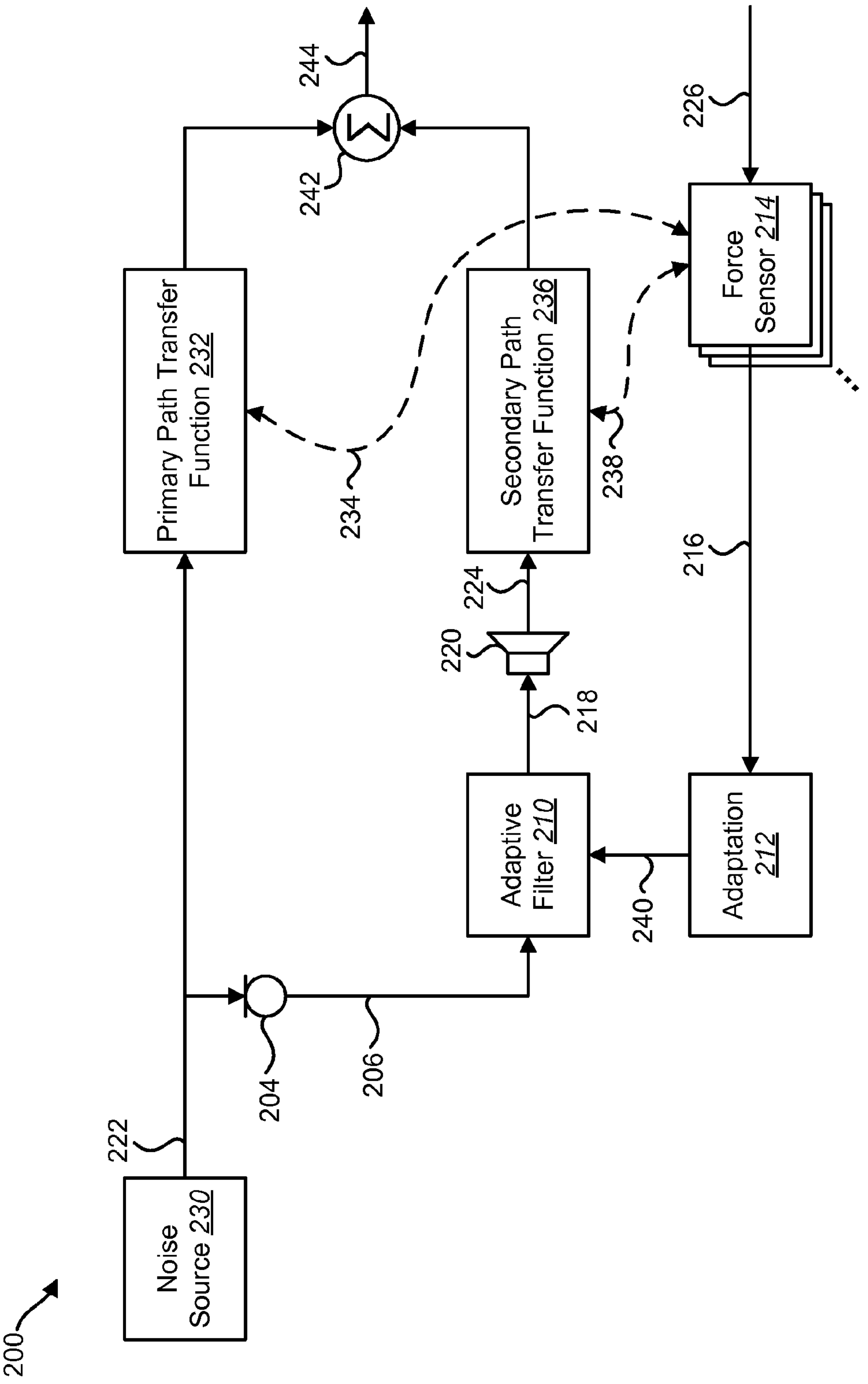
FIG. 2 is a block diagram illustrating one configuration of a model for controlling noise using force.

FIG. 2 is a block diagram illustrating one configuration of a model 200 for controlling noise using force. The model 200 may include a noise source 230, noise microphone 204, a speaker 220, an adaptive filter 210, an adaptation block/module 212, one or more force sensors 214, a first or primary path transfer function 232, a second or secondary path transfer function 236 and/or a summer 242. The noise source 230 may produce an acoustic noise signal 222. For example, the noise source 230 may include environmental (e.g., ambient, background) noise generators such as people, machines, stereos, vehicles, weather, etc.

The noise microphone 204 may be a transducer that converts acoustic noise signals 222 from a noise source 230 into electrical or electronic signals 206. For example, the noise microphone 204 may convert acoustic noise signals 222 (e.g., environmental noise, background noise, ambient noise, etc.) from the noise source 230 into an electrical or electronic noise signal 206. The noise signal 206 may be represented as a discrete-time signal $x(n)$ (or $X(z)$ in a complex frequency-domain representation). The noise signal 206 may be provided to the adaptive filter 210, which may be represented as $W(z)$. The adaptive filter output signal 218 may be provided to the speaker 220, which may produce an acoustic noise control signal 224.

The model 200 may include one or more force sensors 214. Some examples of force sensors 214 include capacitive force sensors, piezoelectric force sensors, piezoresistive strain gauges, electromagnetic force sensors, optical force sensors, potentiometric force sensors, etc. The one or more force sensors 214 may be used to detect a force 226. For example, a user may press his/her ear and/or face onto an electronic device that includes the force sensor(s) 214. The one or more force sensors 214 may detect the force 226 between the user's ear (and/or face) and the electronic device. For instance, the one or more force sensors 214 may generate a force signal 216 based on the force 226 detected. The force or pressure signal 216 (denoted R) may indicate the force 226 detected by the force sensor(s) 214. For instance, the force signal 216 may indicate a force or pressure measurement in newtons (N) or newtons per a given area. This force signal 216 may be provided to the adaptation block/module 212.

The adaptation block/module 212 may use the force signal 216 to modify or adapt the functioning of the adaptive filter 210. For example, the adaptation block/module 212 may change the frequency response, taps or coefficients of the adaptive filter 210 based on the force signal 216. For instance, the adaptation block/module 212 may provide information or a signal 240 to the adaptive filter 210 such as taps, filter coefficients and/or scaling factors. In one configuration, the adaptation block/module 212 may change the frequency response of the adaptive filter 210 based on the force signal 216.

A first or primary path transfer function (e.g., noise transfer function) 232 may be used to model the transmission of the acoustic noise signal 222 from the noise source 230 to a user. The primary path transfer function 232 may be denoted $P(z)$. For convenience in modeling, it may be assumed that the acoustic noise signal 222 is the same as the noise signal 206 (e.g., $X(z)$). For example, the primary path transfer function 232 may change the acoustic noise signal 222 $X(z)$ to a signal $X(z)P(z)$ that is provided to the summer 242 (at the user's ear, for example).

A secondary path transfer function (e.g., speaker transfer function) 236 may be used to model the transmission of the acoustic noise control signal 224 from the speaker 220 to the user. The secondary path transfer function 236 may be denoted S(z). For example, the secondary path transfer function 236 may change the acoustic noise control signal 224 X(z)W(z) from the speaker 220 to a signal X(z)W(z)S (z) that is provided to the summer 242 (at the user's ear, for example).

The summer output 244 may be an error signal (denoted e(n) in the time domain or E(z) in the frequency domain, for example). The behavior of the model 200 may thus be illustrated according to the equation X(z)P(z)+X(z)W(z)S (z)=E(z). Assuming that the error E(z) is zero (e.g., the noise control signal cancels the noise signal), the adaptive filter W(z) 210 may be illustrated in Equation (4).

$$W(z) = \frac{-P(z)}{S(z)} \tag{4}$$

As illustrated in FIG. 2, a relationship 234 (e.g., correlation) may exist between the primary path transfer function 232 and the force or pressure detected by the force sensor(s) 214. In other words, the primary path transfer function 232 may vary in accordance with the force or pressure detected by the force sensor(s) 214. For example, when a user presses an electronic device more forcefully against his/her ear, the transmission of noise (e.g., acoustic noise signal 222) into the user's ear may diminish. Additionally, the transmission of noise (e.g., the acoustic noise signal 222) may increase into a user's ear as a user presses the electronic device less forcefully against his/her ear.

As illustrated in FIG. 2, a relationship 238 (e.g., correlation) may exist between the secondary path transfer function 236 and the force or pressure detected by the force sensor(s) 214. In other words, the secondary path transfer function 236 may vary in accordance with the force or pressure detected by the force sensor(s) 214. For example, when a user presses an electronic device more forcefully against his/her ear, the transmission of the noise control signal 224 into the user's ear may increase. Additionally, the transmission of the noise control signal 224 may decrease into a user's ear as a user presses the electronic device less forcefully against his/her ear.

Thus, the force signal 216 may be used to adapt the adaptive filter 210 in order to reduce or cancel an acoustic noise signal 222. In one configuration, the primary transfer function P(z) 232 and the secondary transfer function S(z) 236 may be modeled as illustrated in Equations (5) and (6).

$$P(z)=g(R)P_o(z) \tag{5}$$

$$S(z)=h(R)S_o(z) \tag{6}$$

In Equation (5), $P_o(z)$ is a transfer function 232 (e.g., primary path transfer function) at a specific force or pressure, g is a scaling function of a force or pressure value R 216 and z is a complex number. In some configurations, $P_o(z)$ may be referred to as a first or primary base transfer function 232 and may be predetermined (e.g., empirically observed). In Equation (6), $S_o(z)$ is the secondary path transfer function 236 at a specific force or pressure, h is a scaling function of the force or pressure value R 216 and z is a complex number. For example, $S_o(z)$ may be referred to as a second or secondary base transfer function 236 and may be predetermined (e.g., empirically observed). In some configurations, the specific force or pressure may be a minimum force or pressure detected by the force sensor(s) 214 when a user is holding (e.g., pressing) an electronic device to the user's ear/face. Using the transfer functions 232, 236, an optimal adaptive filter 210 may be determined as illustrated in Equation (7).

$$W(z) = \frac{-P(z)}{S(z)} = \frac{-g(R)P_o(z)}{[h(R)S_o(z)]} = F(R, z) \tag{7}$$

In Equation (7), W(z) is the adaptive filter 210 and OR, z) is a frequency response. In this example, the adaptation block/module 212 may determine the scaling factors g and h based on the force or pressure value R 216 in order to determine the optimal adaptive ANC filter 210.

Figure 3:
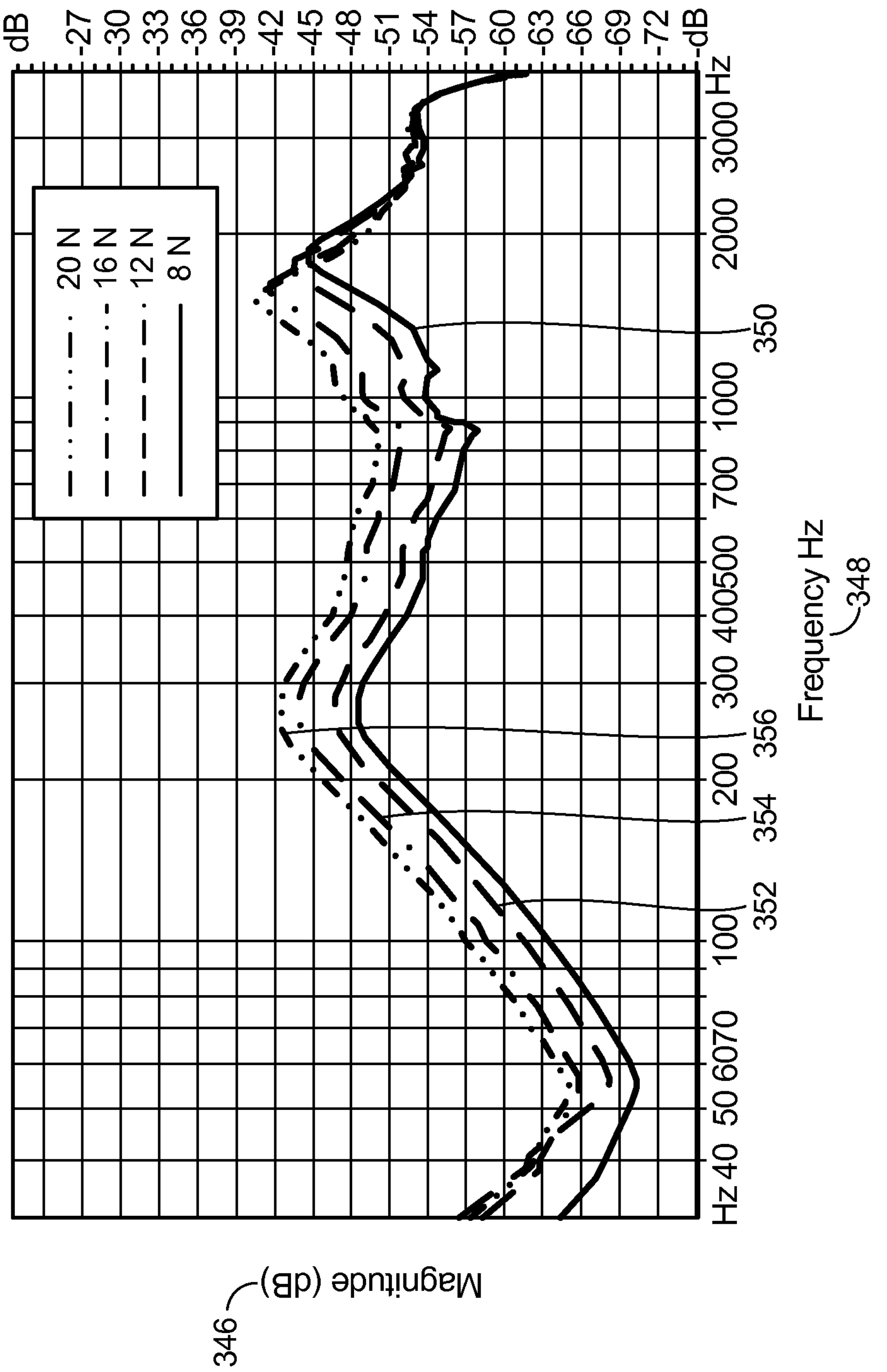
FIG. 3 is a graph illustrating one example of a correspondence between a pressing force and a secondary transfer function.

FIG. 3 is a graph illustrating one example of a correspondence between a pressing force and a secondary transfer function (e.g., S(z)). In FIG. 3, the vertical axis of the graph illustrates a magnitude in decibels (dB) 346 and the horizontal axis of the graph illustrates a frequency in hertz (Hz) 348.

In this example, a first curve 350 illustrates a secondary transfer function (e.g., S(z)) when the pressing force is eight newtons (N). A second curve 352 illustrates the secondary transfer function (e.g., S(z)) when the pressing force is 12 N. A third curve 354 illustrates the secondary transfer function (e.g., S(z)) when the pressing force is 16 N. A fourth curve 356 illustrates the secondary transfer function (e.g., S(z)) when the pressing force is 20 N.

As can be observed from the graph illustrated in FIG. 3, the secondary transfer function (e.g., S(z)) may vary (e.g., correspond or correlate) according to changes in the pressing force. It should be noted that the primary transfer function (e.g., P(z)) may also vary (e.g., correspond or correlate) according to changes in the pressing force.

In accordance with the systems and methods disclosed herein, the pressing force may be used to predict the primary and/or secondary transfer functions. In one configuration, a base transfer function may be scaled depending on the detected force or pressure. For example, the first curve 350 may represent a base secondary transfer function (e.g., $S_o(z)$), which may be a secondary transfer function (e.g., S(z)) at a minimum pressure or force (e.g., a minimum pressure at which a user presses his/her ear and/or face to an electronic device). Based on the pressing force R, a base transfer function may be scaled using a scaling function as illustrated in Equations (5) and (6) above. This may provide approximations for the transfer functions corresponding to the pressing force R.

For instance, if the first curve 350 represents the base secondary transfer function $S_o(z)$, then the secondary transfer function S(z) may be approximated by multiplying the base transfer function $S_o(z)$ by a scaling factor that is determined based on the pressing force R according to a scaling function h(R) as illustrated in Equation (6). For example, assuming that the pressing force is 20 N, the base secondary transfer function $S_o(z)$ may be scaled up (by a scaling function 10)) such that it matches or closely approximates the secondary transfer function S(z) at 20 N. A base primary transfer function $P_o(z)$ may also be scaled based on the pressing force R according to a similar procedure as illustrated in Equation (5) above. The scaled base transfer functions (e.g., $P(z)=g(R)P_o(z)$, $S(z)=h(R)S_o(z)$) may then be used to adjust or determine an adaptive filter W(z) 110.

In another configuration, a range of transfer functions may be predetermined and stored in a lookup table. In this configuration, an electronic device 102 may look up one or more transfer functions based on the pressing force R. For instance, the lookup table may store a range of transfer functions corresponding to a range of detected pressing forces. In this case, the electronic device 102 may look up a primary transfer function P(z) and a secondary transfer function S(z) corresponding to the pressing force R. These transfer functions (e.g., P(z) and S(z)) may then be used to adjust or determine the adaptive filter W(z) 110.

Figure 4:
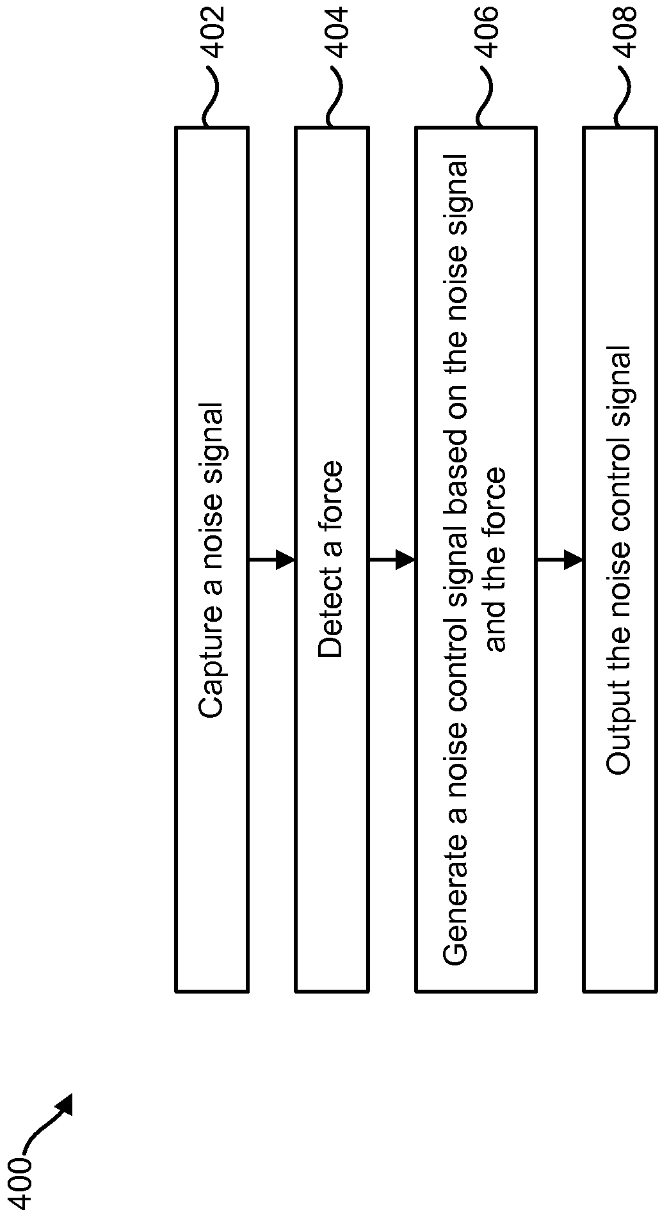
FIG. 4 is a flow diagram illustrating one configuration of a method for controlling noise using force.

FIG. 4 is a flow diagram illustrating one configuration of a method 400 for controlling noise using force or pressure. An electronic device 102 may capture 402 a noise signal 106. For example, the electronic device 102 may use a noise microphone 104 to convert an acoustic noise signal 122 into an electrical or electronic noise signal 106.

The electronic device 102 may detect 404 a force 126. For example, the electronic device 102 may use one or more force sensors 114 to detect a force 126 that is being applied to the electronic device 102. The force 126 detected 404 may be a pressing force between a user's ear (and/or face) and the electronic device 102. In some configurations, the force sensor(s) 114 may produce a force signal 116 based on the detected force 126.

The electronic device 102 may generate 406 a noise control signal 118 based on the noise signal 106 and the force 126. For example, the electronic device 102 may perform active noise control (ANC) based on the noise signal 106 and the force 126 (e.g., a force signal 116 based on the force 126). For instance, the electronic device 102 may use the force signal 116 to adapt or determine an adaptive filter 110. The adaptive filter 110 may then filter the noise signal 106 to generate a noise control signal 118.

The electronic device 102 may output 408 the noise control signal 118. For example, the electronic device 102 may provide the noise control signal 118 to a speaker 120, which may convert the noise control signal 118 from an electrical or electronic signal into an acoustic noise control signal 124. This acoustic noise control signal 124 may be approximately out-of-phase with an acoustic noise signal 122 and may have an amplitude that is approximately the same as the acoustic noise signal 122. Thus, the acoustic noise signal 122 and the acoustic noise control signal 124 may interfere with each other, thus reducing or cancelling the acoustic noise signal 122.

Figure 5:
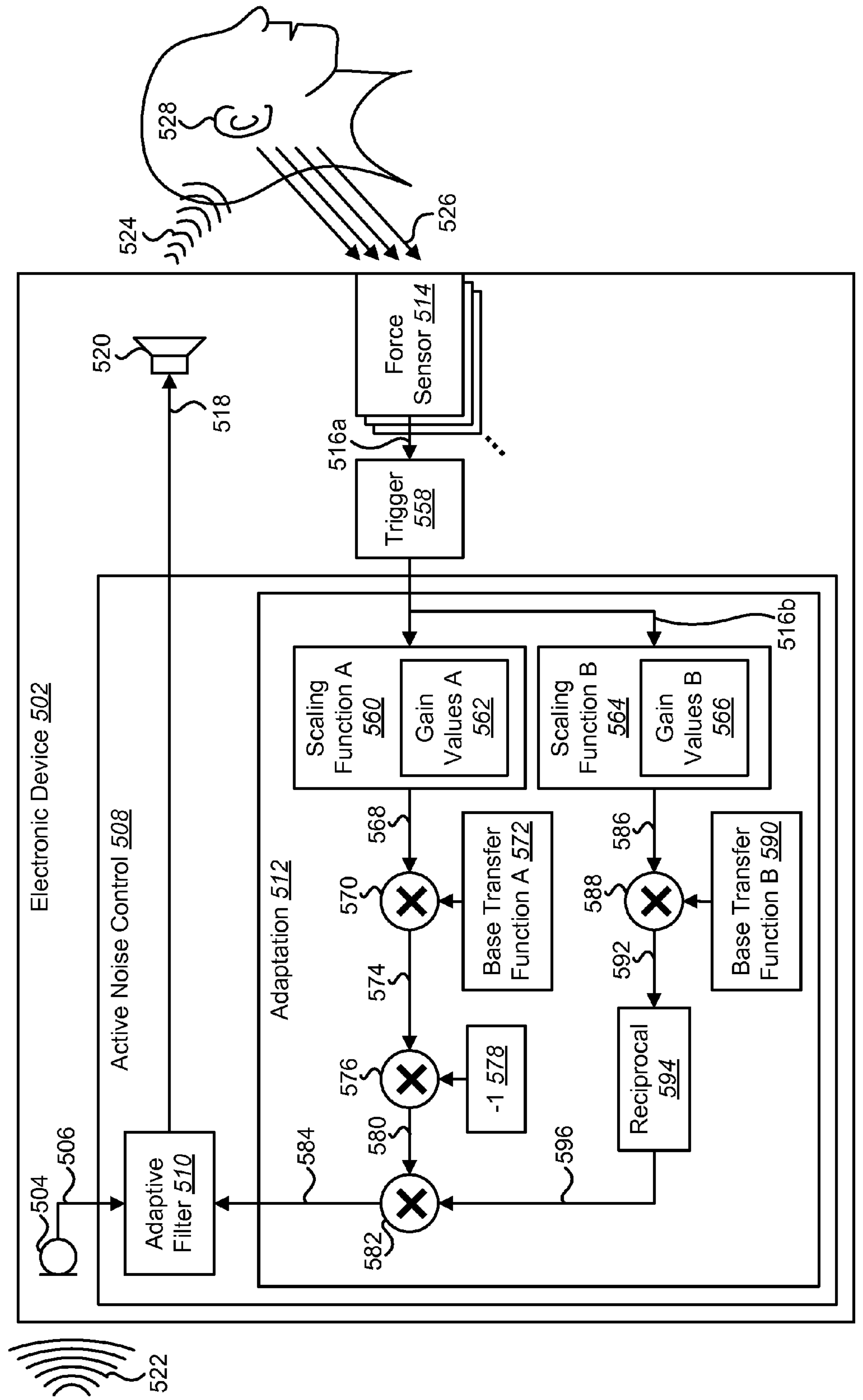
FIG. 5 is a block diagram illustrating a more specific configuration of an electronic device in which systems and methods for controlling noise using force may be implemented.

FIG. 5 is a block diagram illustrating a more specific configuration of an electronic device 502 in which systems and methods for controlling noise using force or pressure may be implemented. The electronic device 502 may include a noise microphone 504, a speaker 520, an active noise control block/module 508, a trigger block/module 558 and/or one or more force sensors 514. In one configuration, the active noise control block/module 508 may be referred to as noise control circuitry.

The noise microphone 504 may be a transducer that converts acoustic signals 522 into electrical or electronic signals 506. For example, the noise microphone 504 may convert acoustic noise signals 522 (e.g., environmental noise, background noise, ambient noise, etc.) into an electrical or electronic noise signal 506. The noise signal 506 may be provided to the active noise control block/module 508.

As mentioned above, the electronic device 502 may include one or more force sensors 514. Some examples of force sensors 514 include capacitive force sensors, piezoelectric force sensors, piezoresistive strain gauges, electromagnetic force sensors, optical force sensors, potentiometric force sensors, etc. The one or more force sensors 514 may be used to detect a force 526 on the electronic device 502. For example, a user may press his/her ear 528 and/or face onto the electronic device 502. The one or more force sensors 514 may detect the force 526 between the user's ear 528 (and/or face) and the electronic device 502. For instance, the one or more force sensors 514 may generate a force signal 516 (e.g., R in Equations (5), (6) and (7)) based on the force 526 placed on the electronic device 502. The force signal 516 may indicate or reflect the force 526 detected by the force sensor(s) 514. For instance, the force signal 516 may indicate a force or pressure measurement in newtons (N). This force signal 516 may be provided to the trigger block/module 558 and/or the active noise control block/module 508.

The trigger block/module 558 may be optionally used in accordance with the systems and methods disclosed herein. The trigger block/module 558 may use a force signal **516*a* from the force sensor(s) 514 to determine a selected force signal 516*b*. In one configuration, the trigger block/module 558 may be configured to provide a force signal 516*a* as a selected force signal 516*b* when the force signal 516*a* changes a given amount. In other words, the trigger block/module 558 may only update the selected force signal 516*b* if the force signal 516*a* increases or decreases a certain amount. The trigger block/module 558 may have a quantizing effect on the force signal 516*a*. For example, the trigger block/module 558 may only provide a selected force signal 516*b* at a discrete number of levels. Additionally or alternatively, the trigger block/module 558 may update the selected force signal 516*b*** at a particular frequency.

The active noise control block/module 508 may use the noise signal 506 and the force signal 516 (e.g., R) to generate a noise control signal 518. For example, the noise control signal 518 may be used to reduce or cancel the acoustic noise signal 522. For instance, the noise control signal 518 may be provided to a speaker 520 that converts the noise control signal 518 into an acoustic noise control signal 524. The acoustic noise control signal 524 may have an amplitude that is similar to the acoustic noise signal 522 and may be approximately out-of-phase with the acoustic noise signal 522. In this way, the acoustic noise control signal 524 may interfere with the acoustic noise signal 522, thereby reducing or cancelling the acoustic noise signal 522. Thus, the acoustic noise signal 522 may be reduced and/or effectively eliminated as perceived by a user of the electronic device 502.

In one configuration, the active noise control block/module 508 may include an adaptive filter 510 and an adaptation block/module 512. The adaptation block/module 512 may use the force signal 516 to modify or adapt the functioning of the adaptive filter 510. For example, the adaptation block/module 512 may change the frequency response, taps or coefficients of the adaptive filter 510 based on the force signal 516.

In one configuration, the adaptation block/module 512 may include scaling function A 560 and scaling function B 564. Scaling function A 560 may be one example of g(R) illustrated in Equations (5) and (7) above. Scaling function A 560 may include or generate gain values A 562. For example, scaling function A 560 may use a lookup table that includes gain values A 562. For instance, scaling function A (e.g., g(R)) 560 may look up a particular gain value from gain values A 562 to be applied to base transfer function A 572 based on the force signal (e.g., R) 516. In another configuration, scaling function A 560 may determine a gain value 568 based on some other function or algorithm. The gain value 568 determined according to scaling function A 560 may be provided to a multiplier 570.

The multiplier 570 may multiply the gain value 568 by base transfer function A 572. Base transfer function A 572 is one example of the base primary (path) transfer function $P_o(z)$ illustrated in Equations (5) and (7) above. The product 574 of base transfer function A 572 and the gain value (e.g., $g(R)P_o(z)$)) may be multiplied by −1 578 by a multiplier 576. This product (e.g., $-g(R)P_o(z)$)) 580 may be provided to another multiplier 582.

Scaling function B 564 may be one example of h(R) illustrated in Equations (6) and (7) above. Scaling function B 564 may include or generate gain values B 566. For example, scaling function B 564 may use a lookup table that includes gain values B 566. For instance, scaling function B (e.g., h(R)) 564 may look up a particular gain value from gain values B 566 to be applied to base transfer function B 590 based on the force signal (e.g., R) 516. In another configuration, scaling function B 564 may determine a gain value 586 based on some other function or algorithm. The gain value 586 determined according to scaling function B 564 may be provided to a multiplier 588.

The multiplier 588 may multiply the gain value 586 by base transfer function B 590. Base transfer function B 590 is one example of the base secondary (path) transfer function $S_o(z)$ illustrated in Equations (6) and (7) above. The product 592 of base transfer function B 590 and the gain value (e.g., $h(R)S_o(z)$)) may be provided to a reciprocal block/module 594, which may determine the reciprocal $$\left(\text{e.g., } \frac{1}{[h(R)S_o(z)]}\right) 596$$

of the product 592. This reciprocal 596 may be multiplied by the product (e.g., $-g(R)P_o(z)$)) 580 by a multiplier 582. The resulting product $$\left(\text{e.g., } \frac{-g(R)P_o(z)}{[h(R)S_o(z)]}\right) 584$$

may be used to adapt or determine the adaptive filter 510. For example, the adaptive filter 510 or its coefficients, taps and/or frequency response $$\left(\text{e.g., } W(z) = \frac{-P(z)}{S(z)} = \frac{-g(R)P_o(z)}{[h(R)S_o(z)]} = F(R, z)\right)$$

may be determined based on the resulting product $$\left(\text{e.g., } \frac{-g(R)P_o(z)}{[h(R)S_o(z)]}\right) 584.$$

The adaptive filter 510 may filter the noise signal 506 to produce the noise control signal 518. For example, the adaptive filter 510 may filter the noise signal 506 as determined by the adaptation block/module 512 based on the force signal 516. The noise control signal 518 may be provided to the speaker 520 in order to reduce and/or cancel the acoustic noise signal 522 as described above.

Figure 6:
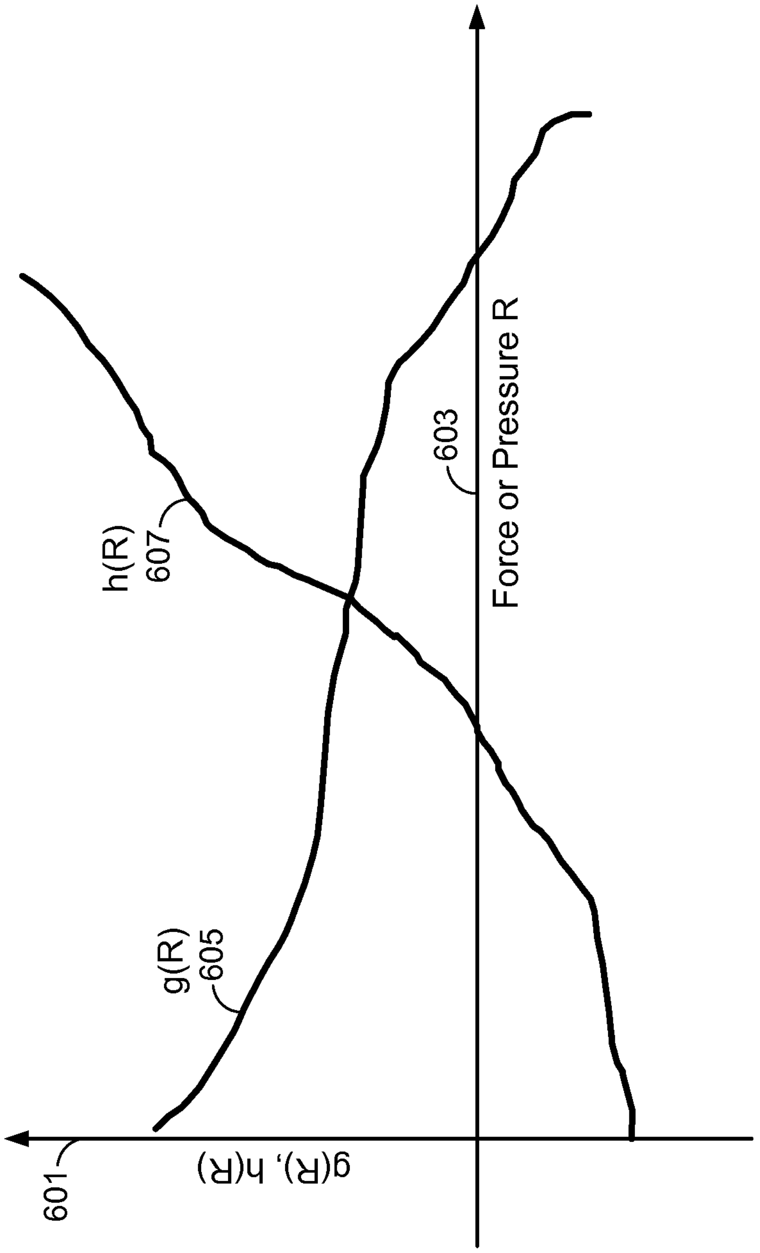
FIG. 6 is a graph illustrating one example of scaling functions.

FIG. 6 is a graph illustrating one example of scaling functions. The vertical axis 601 in the graph illustrated in FIG. 6 shows a magnitude or gain value of scaling functions g(R) 605 and h(R) 607. The functions g(R) 605 and h(R) 607 may be examples of g(R) and h(R) illustrated in Equations (1), (2), (5) and (6). The horizontal axis 603 in the graph illustrates a force or pressure R in newtons (N). An example of a first scaling function g(R) 605 is illustrated as decreasing in magnitude as force or pressure R increases. Conversely, an example of a second scaling function h(R) 607 is illustrated as increasing in magnitude as force or pressure R increases. As the force or pressure R increases, the magnitudes or gains determined by the scaling functions may behave approximately as illustrated. These magnitudes or gains may be applied to base transfer functions in order to determine or adapt an adaptive filter as described above (e.g., as illustrated in Equation (7)).

Figure 7:
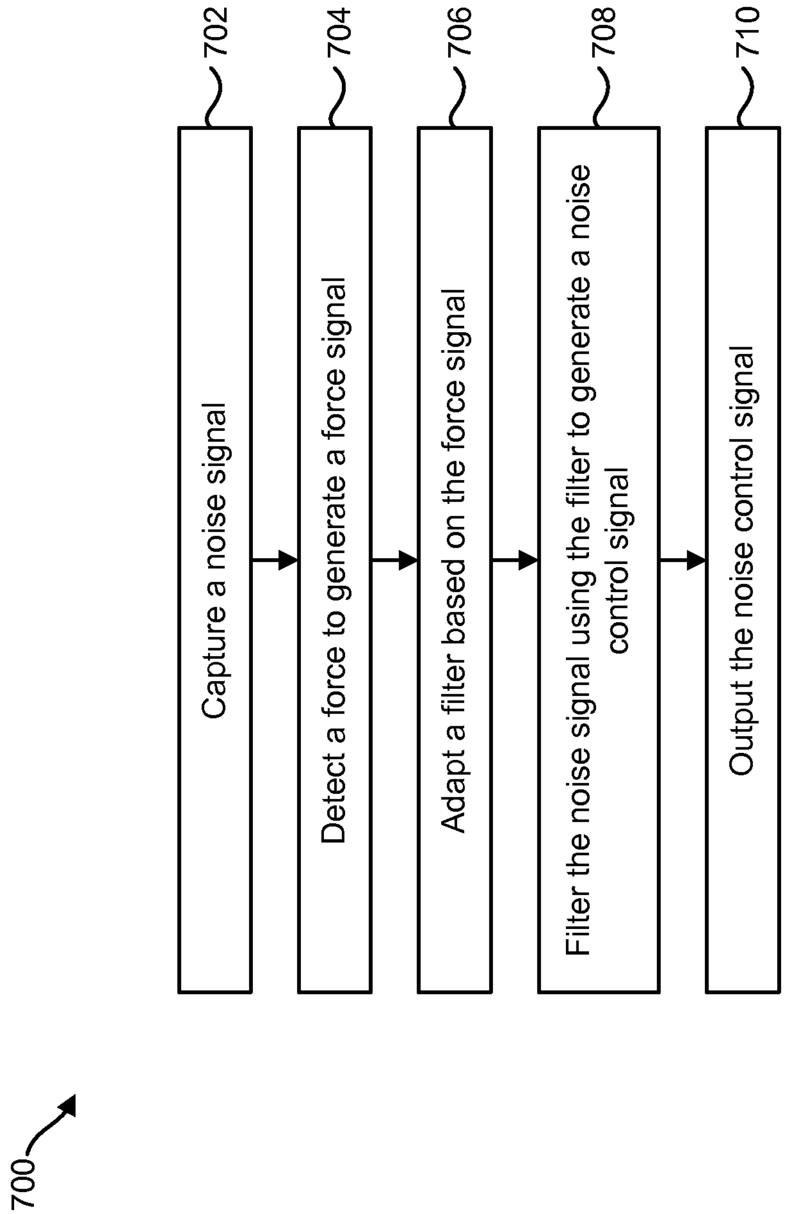
FIG. 7 is a flow diagram illustrating a more specific configuration of a method for controlling noise using force.

FIG. 7 is a flow diagram illustrating a more specific configuration of a method 700 for controlling noise using force. An electronic device 102 may capture 702 a noise signal 106. For example, the electronic device 102 may use a noise microphone 104 to convert an acoustic noise signal 122 into an electrical or electronic noise signal 106.

The electronic device 102 may detect 704 a force 126 to generate a force signal 116. For example, the electronic device 102 may use one or more force sensors 114 to detect a force 126 that is being applied to the electronic device 102. The force 126 detected 704 may be a pressing force between a user's ear 128 (and/or face) and the electronic device 102. The force sensor(s) 114 may detect and/or measure a force 126 based on a change in resistivity, capacitance, electromagnetic fields, charge, potential and/or optics, for example. The force 126 detected 704 and/or measured may be in relation to an electronic device panel, touchscreen, speaker and/or other part(s) of the electronic device 102. The force sensor(s) 114 may produce a force signal 116 based on the detected force 126. For instance, the force signal 116 may indicate a pressing force R (in newtons, for example).

The electronic device 102 may adapt 706 a filter based on the force signal 116. For example, the electronic device 102 may change the frequency response of an adaptive filter 110 based on the force signal 116. In one configuration, the electronic device 102 may determine one or more gain values based on the force signal 116 using one or more scaling functions. The one or more gain values may be used to scale one or more base transfer functions. The scaled base transfer function(s) may then be used to adapt 706 the filter.

Additionally or alternatively, the electronic device 102 may determine one or more transfer functions based on the force signal 116. For example, the electronic device 102 may look up one or more transfer functions from a lookup table based on the force signal 116. The one or more transfer functions may then be used the adapt 706 the filter.

The electronic device 102 may filter 708 the noise signal 106 using the filter to generate a noise control signal 118. For example, filtering 708 the noise signal 106 using the adapted 706 filter may generate or produce a noise control signal 118. This may facilitate active noise control (ANC) based on the noise signal 106 and the force 126 (e.g., a force signal 116 based on the force 126). Filtering 708 the noise signal 106 may be accomplished using a digital filter (e.g., a processor, digital circuitry, etc.) or may be accomplished using an analog filter. For example, the adaptive filter 110 may be implemented in hardware, software or a combination of both. In one example, digital samples of the noise signal 106 may be provided to a processor, which may perform mathematical operations on the noise signal 106 using a digital filter to produce the noise control signal 118. In another example, the noise signal 106 may be provided to an analog implementation of the adaptive filter 110, which may produce the noise control signal 118 using the noise signal 106.

The electronic device 102 may output 710 the noise control signal 118. For example, the electronic device 102 may provide the noise control signal 118 to a speaker 120, which may convert the noise control signal 118 from an electrical or electronic signal into an acoustic noise control signal 124. This acoustic noise control signal 124 may be approximately out-of-phase with an acoustic noise signal 122 and may have an amplitude that is approximately the same as the acoustic noise signal 122. Thus, the acoustic noise signal 122 and the acoustic noise control signal 124 may interfere with each other, thus reducing or cancelling the acoustic noise signal 122.

Figure 8:
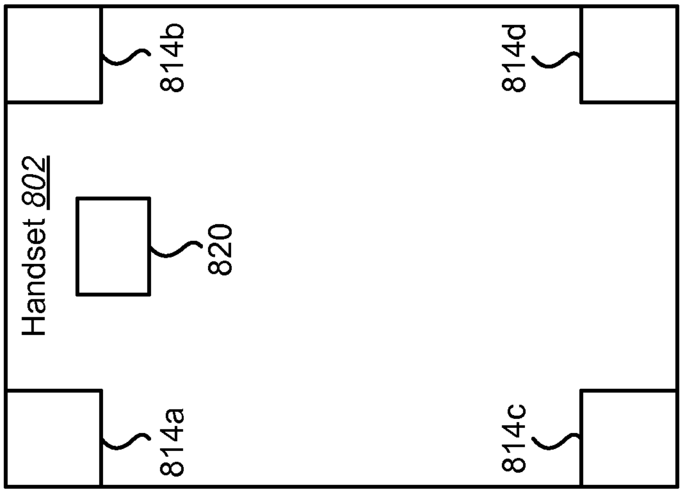
FIG. 8 is a block diagram illustrating one configuration of force sensors in a handset.

FIG. 8 is a block diagram illustrating one configuration of force sensors 814*a-d* in a handset 802. Examples of the handset 802 include electronic devices, such as cellular phones, smartphones, music players, digital cameras, digital camcorders, personal digital assistants (PDAs), tablet devices, etc. As described above, examples of the force sensors 814*a-d* include capacitive force sensors, piezoelectric force sensors, piezoresistive strain gauges, electromagnetic force sensors, optical force sensors, potentiometric force sensors, etc. In the configuration illustrated in FIG. 8, a speaker 820 may be located near the top of the handset 802. Four force sensors 814*a-d* may be located in or near (e.g., proximate to) the corners of the handset 802. For example, the force sensors 814*a-d* may be integrated into a panel (e.g., screen, touchscreen, housing, keypad, etc.) of the handset 802. Additionally or alternatively, the force sensors 814*a-d* may be located beneath a handset 802 panel (e.g., screen, touchscreen, housing, keypad, etc.). The force sensors 814*a-d* may detect and/or measure a force applied to the handset 802. For example, the force sensors 814*a-d* may detect and/or measure a deflection of a (front and/or back) handset 802 panel. This may occur when a user holds the handset 802 to his/her ear and/or face.

Figure 9:
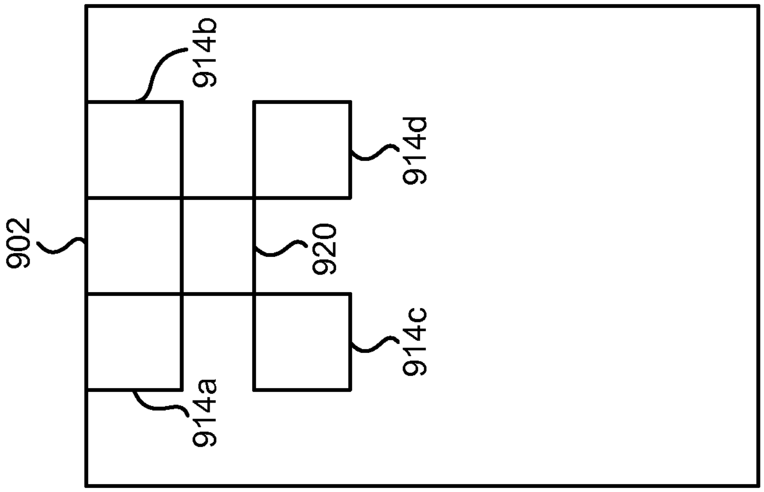
FIG. 9 is a block diagram illustrating another configuration of force sensors in a handset.

FIG. 9 is a block diagram illustrating another configuration of force sensors 914*a-d* in a handset 902. Examples of the handset 902 include electronic devices, such as cellular phones, smartphones, music players, digital cameras, digital camcorders, personal digital assistants (PDAs), tablet devices, etc. As described above, examples of the force sensors 914*a-d* include capacitive force sensors, piezoelectric force sensors, piezoresistive strain gauges, electromagnetic force sensors, optical force sensors, potentiometric force sensors, etc. In the configuration illustrated in FIG. 9, a speaker 920 may be located near the top of the handset 902. Four force sensors 914*a-d* may be located peripherally near (e.g., proximate to) the speaker 920. For example, the force sensors 914*a-d* may be integrated into a panel (e.g., screen, touchscreen, housing, keypad, etc.) of the handset 902 near the speaker 920. Additionally or alternatively, the force sensors 914*a-d* may be located beneath a handset 902 panel (e.g., screen, touchscreen, housing, keypad, etc.). The force sensors 914*a-d* may detect and/or measure a force applied to the handset 902. For example, the force sensors 914*a-d* may detect and/or measure a deflection of a (front and/or back) handset 902 panel. This may occur when a user holds the handset 902 to his/her ear and/or face.

Figure 10:
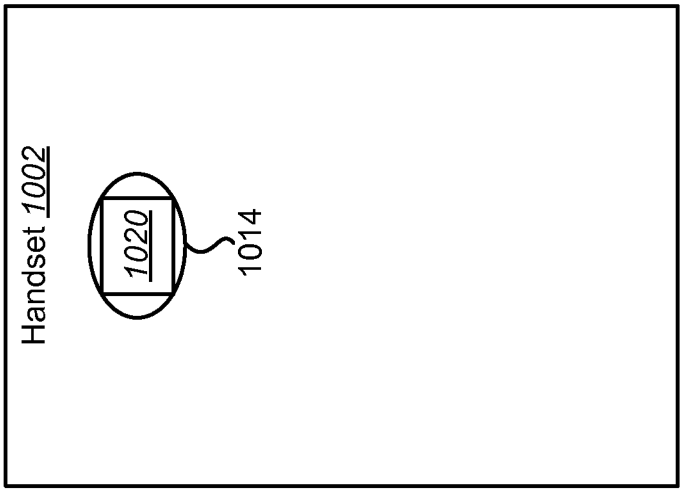
FIG. 10 is a block diagram illustrating one configuration of a force sensor in a handset.

FIG. 10 is a block diagram illustrating one configuration of a force sensor 1014 in a handset 1002. Examples of the handset 1002 include electronic devices, such as cellular phones, smartphones, music players, digital cameras, digital camcorders, personal digital assistants (PDAs), tablet devices, etc. As described above, examples of the force sensor 1014 include capacitive force sensors, piezoelectric force sensors, piezoresistive strain gauges, electromagnetic force sensors, optical force sensors, potentiometric force sensors, etc. In the configuration illustrated in FIG. 10, a speaker 1020 may be located near the top of the handset 1002. A single gasket-type force sensor 1014 may be located with (e.g., around) the speaker 1020. For example, the force sensor 1014 may be integrated into a panel (e.g., screen, touchscreen, housing, keypad, etc.) of the handset 1002 around the speaker 1020. Additionally or alternatively, the force sensor 1014 may be located beneath a handset 1002 panel (e.g., screen, touchscreen, housing, keypad, etc.) around the speaker 1020. The force sensor 1014 may detect and/or measure a force applied to the speaker 1020 and/or handset 1002. For example, the force sensor 1014 may detect and/or measure a deflection of the speaker 1020 into the handset 1002. This may occur when a user holds the handset 1002 to his/her ear and/or face.

Figure 11:
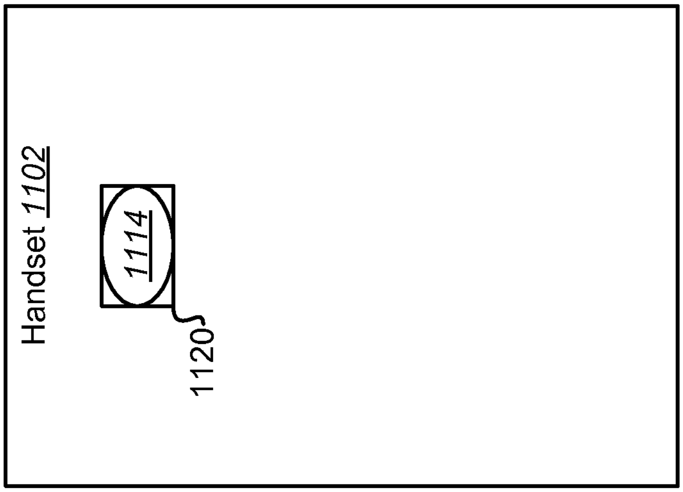
FIG. 11 is a block diagram illustrating another configuration of a force sensor in a handset.

FIG. 11 is a block diagram illustrating another configuration of a force sensor 1114 in a handset 1102. Examples of the handset 1102 include electronic devices, such as cellular phones, smartphones, music players, digital cameras, digital camcorders, personal digital assistants (PDAs), tablet devices, etc. As described above, examples of the force sensor 1114 include capacitive force sensors, piezoelectric force sensors, piezoresistive strain gauges, electromagnetic force sensors, optical force sensors, potentiometric force sensors, etc. In the configuration illustrated in FIG. 11, a speaker 1120 may be located near the top of the handset 1102. A single force sensor 1114 may be located behind or beneath the speaker 1120. For example, the force sensor 1114 may placed behind the speaker 1120 in the handset 1102. The force sensor 1114 may detect and/or measure a force applied to the speaker 1120 and/or handset 1102. For example, the force sensor 1114 may detect and/or measure a deflection of the speaker 1120 into the handset 1102. This may occur when a user holds the handset 1102 to his/her ear and/or face. It should be noted that although several configurations of one or more force sensors are illustrated in FIGS. 8, 9, 10 and 11, other configurations may be used in accordance with the systems and methods disclosed herein.

Figure 12:
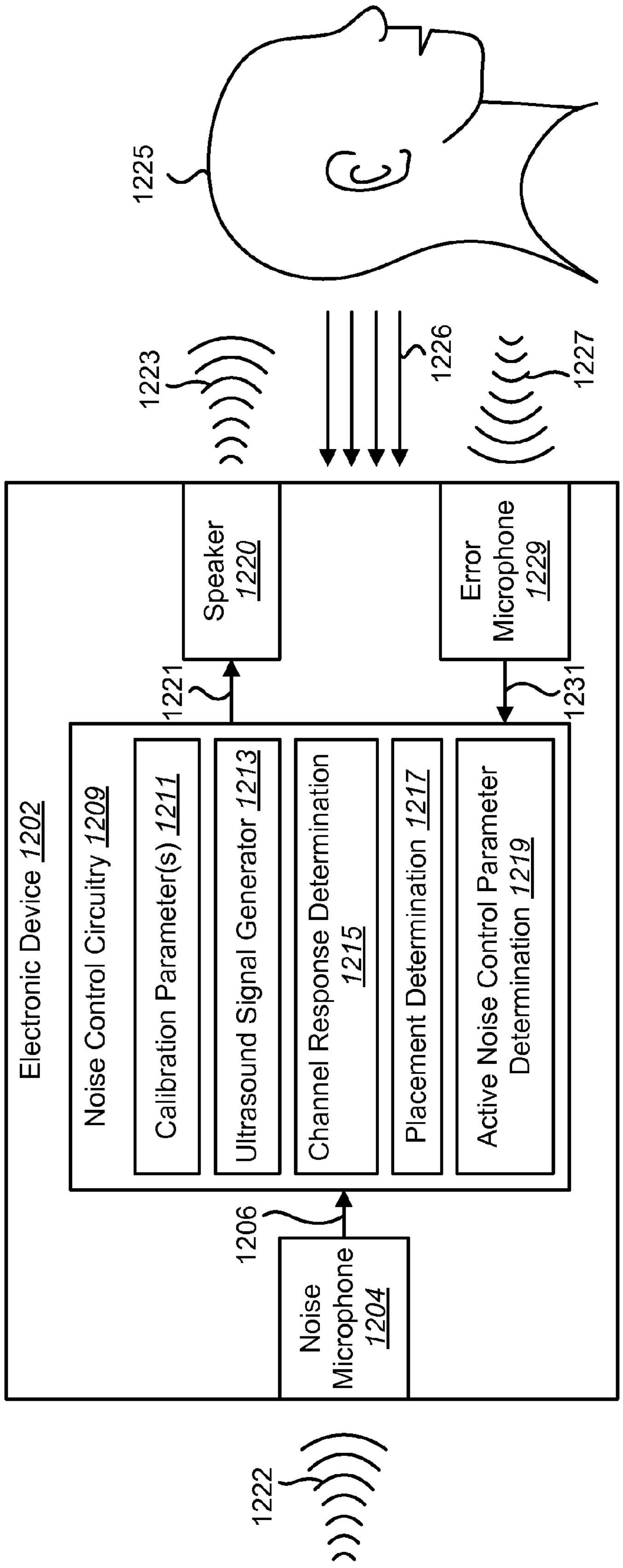
FIG. 12 is a block diagram illustrating one configuration of an electronic device in which systems and methods for controlling noise may be implemented.

FIG. 12 is a block diagram illustrating one configuration of an electronic device 1202 in which systems and methods for controlling noise may be implemented. The electronic device 1202 may include one or more noise microphones 1204, one or more speakers 1220, one or more error microphones 1229 and noise control circuitry 1209. One or more of the elements included within the electronic device 1202 may be implemented in hardware, software or a combination of both. For example, the noise control circuitry 1209 may be implemented in hardware, software or a combination of both.

The noise microphone 1204 may be a transducer that converts acoustic noise signals 1222 into electrical or electronic noise signals 1206. For example, the noise microphone 1204 may convert acoustic noise signals 1222 (e.g., environmental noise, background noise, ambient noise, etc.) into an electrical or electronic noise signal 1206. It should be noted that one or more noise microphones 1204 may be used. The one or more noise microphones 1204 may be placed in a variety of locations on the electronic device 1202. For example, one or more noise microphones 1204 may be placed on the back of a handset/headset, on one or more sides of a handset/headset, etc. The noise signal 1206 may be provided to the noise control circuitry 1209.

The electronic device 1202 includes one or more error microphones 1229. The one or more error microphones 1229 receive acoustic channel signals 1227. For example, the error microphone 1229 receives ultrasound channel signals. Additionally or alternatively, the error microphone 1229 may receive remaining portions of the noise signal 1222 (that have not been cancelled, for example). The error microphone(s) 1229 may convert the acoustic signals received or captured into electrical or electronic channel signals 1231, which may be provided to the noise control circuitry 1209.

The electronic device 1202 includes one or more speakers 1220. The one or more speakers 1220 may convert an electrical or electronic signal 1221 into an acoustic signal 1223. For example, the electrical or electronic signal 1221 may include an electronic noise control signal and/or an electronic ultrasound signal. The speaker(s) 1220 may output an acoustic signal 1223 based on the electrical or electronic signal 1221. For example, the speaker 1220 may output an acoustic ultrasound signal and/or an acoustic noise control signal. Accordingly, the acoustic signal 1223 may include an acoustic ultrasound signal, an acoustic noise control signal or a combination of both. Additionally or alternatively, the speaker(s) 1220 may output other acoustic signals (e.g., voice, music and/or other acoustic signals, etc.). In some configurations, the speaker 1220 may be an earpiece and the error microphone 1229 may be located nearby the speaker 1220.

The noise control circuitry 1209 may include an ultrasound signal generator 1213, a channel response determination block/module 1215, a placement determination block/module 1217 and/or an active noise control parameter determination block/module 1219. The noise control circuitry 1209 may be coupled to the noise microphone(s) 1204, to the error microphone(s) 1229 and to the speaker(s) 1220.

The noise control circuitry 1209 may operate in a calibration stage or mode and a runtime stage or mode. For simplicity, the calibration stage or mode may be referred to as "calibration" and the runtime stage or more may be referred to as "runtime" herein. During calibration, the noise control circuitry 1209 determines one or more calibration parameters 1211. Examples of calibration parameters 1211 include one or more active noise control parameters, one or more calibration channel response parameters (e.g., channel response statistics). Each calibration parameter 1211 or set of calibration parameters 1211 may correspond to a calibration placement, which is described in greater detail below.

In some configurations, calibration may occur as follows. The electronic device 1202 may determine to perform a calibration cycle. The electronic device 1202 may determine one or more calibration active noise control parameters. Examples of active noise control parameters include filter coefficients, transfer functions, filter taps and/or one or more filter characteristics (e.g., frequency response, magnitude response, phase response, etc.).

The electronic device 1202 may output a calibration ultrasound signal. For example, the ultrasound signal generator 1213 may provide an electronic ultrasound signal to the speaker 1220, which may output the calibration ultrasound signal. The electronic device 1202 may receive a calibration ultrasound channel signal. For example, the acoustic channel signal 1227 may include an acoustic calibration ultrasound channel signal, which may be received by the error microphone 1229, converted to an electronic calibration ultrasound channel signal and provided to the noise control circuitry 1209.

The electronic device 1202 may determine one or more calibration channel response parameters based on the calibration ultrasound channel signal. For example, the channel response determination block/module 1215 may determine calibration channel response parameters (e.g., calibration channel response statistics) based on the calibration ultrasound channel signal. One or more of the calibration parameters 1211 (e.g., calibration channel response parameter(s) and/or active noise control parameter(s)) may be stored for use during runtime.

One or more of these calibration procedures may be repeated for various calibration placements. For example, each calibration parameter 1211 or set of calibration parameters 1211 determined may correspond to a particular calibration placement of the electronic device 1202. A placement may be or may depend on one or more of holding force, position, location, orientation, pressing force 1226 between the electronic device 1202 and a user 1225 or user model 1225 (e.g., HATS) and coupling (e.g., sealing) between the electronic device 1202 and a user 1225 or user model 1225 (e.g., HATS). In some configurations, the electronic device 1202 (e.g., ANC device) may be mounted next to a user model 1225 (e.g., HATS) during calibration.

It should be noted that while a placement may be or may depend on one or more of the foregoing factors, direct measurement of one or more of these factors may not be required in some configurations of the systems and methods disclosed herein. For instance, a holding force may not be directly measured. However, the holding force may correlate with one or more channel response parameters (e.g., statistics), which may be determined (e.g., measured) based on outputting an ultrasound signal and receiving an ultrasound channel signal. Accordingly, as used herein, the term "calibration placement" may refer to or correspond to a placement during calibration and/or may refer to or correspond to one or more calibration parameters 1211 (e.g., calibration active noise control parameter(s) and/or calibration ultrasound channel response parameter(s)) determined that correspond to a placement of the electronic device 1202 during calibration. Thus, while a placement (depending on one or more of holding force, position, location, orientation, pressing force and/or coupling, for example) may or may not be directly measured during calibration, a "calibration placement" may refer to one or more calibration parameters 1211 determined during a calibration cycle corresponding to a particular placement. It should also be noted that a "runtime placement" may be determined based on one or more calibration placements (e.g., calibration parameter(s) 1211), even though one or more of the holding force, position, location, orientation, pressing force and/or coupling may or may not be directly measured during runtime. Additionally or alternatively, a "runtime placement" may refer to or correspond to a placement during runtime and/or may refer to or correspond to one or more runtime parameters (e.g., runtime channel response parameter(s)).

During runtime (when the electronic device 1202 is in use, for example), the electronic device 1202 may output a runtime ultrasound signal. For example, the ultrasound signal generator 1213 may provide an electronic ultrasound signal to the speaker 1220, which may output the runtime ultrasound signal. The electronic device 1202 may receive a runtime ultrasound channel signal. For example, the acoustic channel signal 1227 may include an acoustic runtime ultrasound channel signal, which may be received by the error microphone 1229, converted to an electronic runtime ultrasound channel signal and provided to the noise control circuitry 1209.

The electronic device 1202 may determine one or more runtime channel response parameters based on the runtime ultrasound channel signal. For example, the channel response determination block/module 1215 may determine runtime channel response statistics based on the runtime ultrasound channel signal.

The electronic device 1202 may determine a runtime placement based on the one or more runtime channel response parameters and the one or more calibration parameters. For example, the placement determination block/module 1217 may determine a runtime placement by selecting calibration channel response parameters (corresponding to a particular calibration placement) that are similar to (e.g., most similar to) the runtime channel response parameters. Additionally or alternatively, the placement determination block/module 1217 may determine a runtime placement by selecting a range of calibration channel response parameters. For instance, the placement determination block/module 1217 may select calibration channel response statistics neighboring the runtime channel response statistics (e.g., that are nearest to, greater than and/or less than the runtime channel response statistics). Thus, the electronic device 1202 may deduce (e.g., select, interpolate and/or extrapolate) a runtime placement that is similar to a calibration placement corresponding to one or more calibration parameters.

The electronic device 1202 may determine one or more runtime active noise control parameters based on the runtime placement. In one example, the runtime placement may correspond to a selected calibration placement with calibration channel response parameters similar to the runtime channel response parameters. In this example, the runtime active noise control parameter(s) may be selected from calibration active noise control parameter(s) corresponding to the selected calibration placement. In other examples, the one or more runtime active noise control parameter(s) may be interpolated or extrapolated from a range of calibration active noise control parameters corresponding to calibration placements. For instance, runtime calibration active noise control parameters may be interpolated from a range of calibration active noise control parameters corresponding to calibration placements with calibration channel response parameters neighboring the runtime channel response parameters (that correspond to the runtime placement).

The noise control circuitry 1209 may generate a noise control signal based on the noise signal 1206 and the runtime active noise control parameter(s). For example, the noise control signal may be used to reduce or cancel the acoustic noise 1222. For instance, the noise control signal (which may be part or all of the signal 1221, for example) may be provided to a speaker 1220 that converts the noise control signal into an acoustic noise control signal (which may be part or all of the acoustic signal 1223, for example). In some configurations, the speaker 1220 may output the acoustic noise control signal and the acoustic ultrasound signal. In other configurations, the speaker 1220 may output the acoustic noise control signal and the acoustic ultrasound signal in addition to one or more other acoustic signals (e.g., music, speech, etc.). For example, the speaker 1220 may be an earpiece speaker on a cellular phone. It should be noted that one or more speakers 1220 may be used.

The acoustic noise control signal may have a magnitude that is similar to the acoustic noise signal 1222 and may be approximately out-of-phase with the acoustic noise signal 1222. In this way, the acoustic noise control signal may interfere with the acoustic noise signal 1222, thereby reducing or cancelling the acoustic noise signal 1222. Thus, the acoustic noise signal 1222 may be reduced and/or effectively eliminated as perceived by a user 1225 of the electronic device 1202.

In some configurations, the noise control circuitry 1209 may additionally include an adaptive filter and an adaptation block/module (not shown in FIG. 12). The adaptation block/module may modify or adapt the functioning of the adaptive filter. For example, the adaptation block/module may change the frequency response, taps or coefficients of the adaptive filter based on the runtime active noise control parameter(s). For instance, one or more transfer functions may model the transmission of the acoustic noise signal 1222 and the acoustic noise control signal. The one or more transfer functions may be adjusted based on the runtime active noise control parameters in order to adapt the adaptive filter. The adaptive filter may filter the noise signal 1206 to produce the noise control signal. For example, the adaptive filter may filter the noise signal 1206 as determined by the adaptation block/module based on the runtime active noise control parameter(s).

Figure 13:
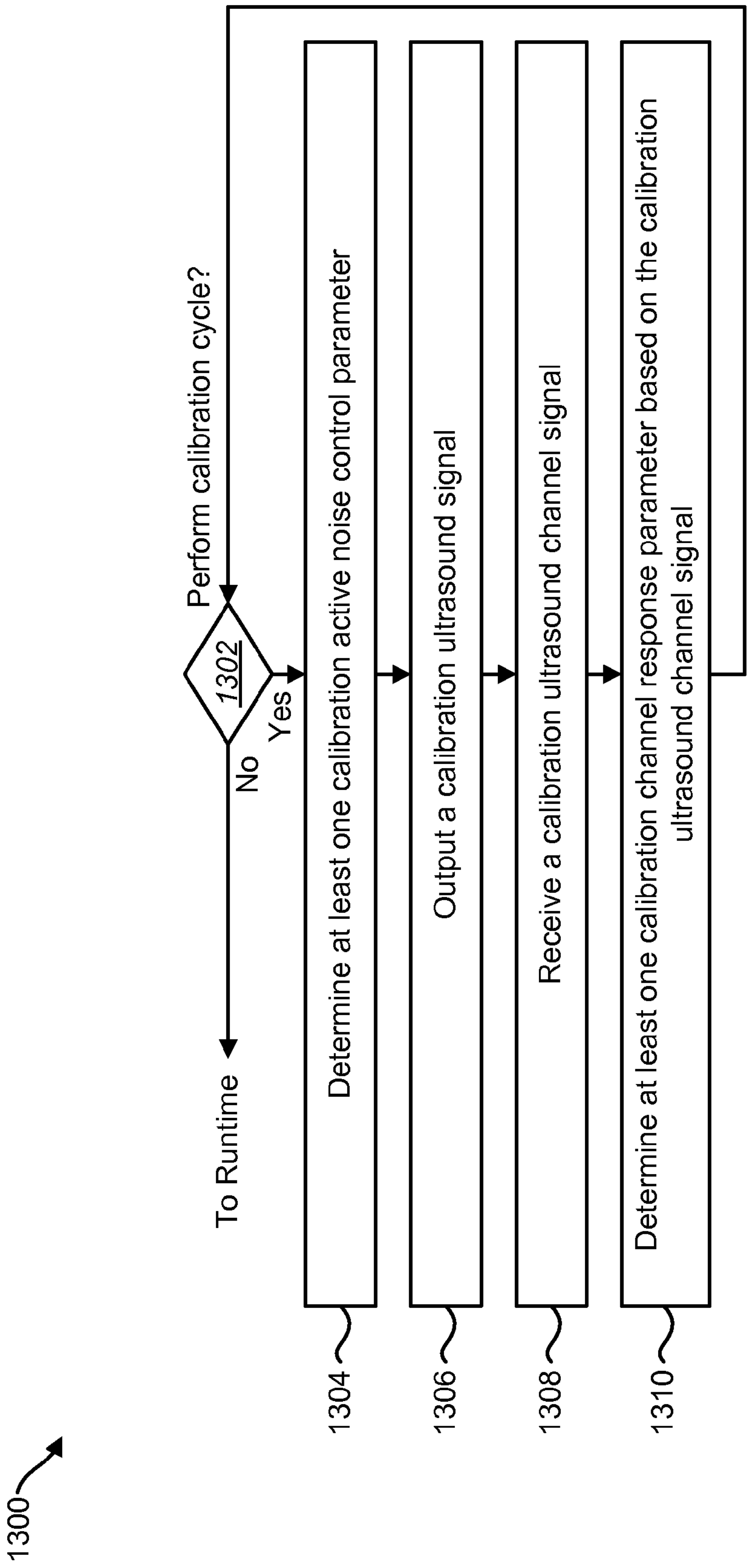
FIG. 13 is a flow diagram illustrating one configuration of a method for determining at least one calibration parameter by an electronic device.

FIG. 13 is a flow diagram illustrating one configuration of a method 1300 for determining at least one calibration parameter 1211 by an electronic device 1202. The electronic device 1202 may determine 1302 whether to perform a calibration cycle. In some configurations, the electronic device 1202 determines 1302 whether to perform a calibration cycle based on a one or more factors. In some configurations, the electronic device 1202 may receive a signal or an indication to perform or to not perform a calibration cycle. For example, the electronic device 1202 may receive a signal (through a wired or wireless transmission medium, for instance) with an indicator directing performance of a calibration cycle or not to perform a calibration cycle (e.g., that calibration has currently ended). In another example, the electronic device 1202 may receive a button press or sensor input that indicates performance or not of a calibration cycle. Additionally or alternatively, the electronic device 1202 may determine 1302 whether to perform a calibration cycle based on whether a threshold number of calibration cycles have already been performed. Additionally or alternatively, the electronic device 1202 may determine 1302 whether to perform a calibration cycle based on one or more calibration parameters 1211. For example, the electronic device 1202 may determine whether the calibration response parameters cover a threshold range to ensure a variety of calibration placements. Additionally or alternatively, the electronic device 1202 may determine 1302 whether to perform a calibration cycle based on whether the electronic device 1202 is in use (e.g., a user has activated the device for a phone call, to listen to music, etc.).

Additional or alternative factors may be employed in determining 1302 whether to perform a calibration cycle. For example, the electronic device 1202 may determine whether its 1202 placement (e.g., position, pressing force, holding force, location and/or orientation, etc.) has changed and/or is stable. For instance, the electronic device 1202 may include one or more accelerometers, tilt sensors, speakers and microphones, timers, pressure sensors and/or cameras, etc., that may be utilized to determine whether its 1202 placement has changed (since a last calibration cycle, for instance) and/or is stable. In one example, whether the placement has changed and/or is stable may be determined based on an ultrasound channel signal. In particular, the electronic device 1202 may output an ultrasound signal, receive an ultrasound channel signal, determine a channel response and determine whether the placement has changed and/or is stable based on the channel response. If the placement has changed and/or if the placement is stable (e.g., the placement is not changing or has changed within a threshold), the electronic device 1202 may determine 1302 to perform a calibration cycle.

Determining 1302 whether to perform a calibration cycle may enable the electronic device 1202 to perform calibration cycles for multiple different calibration placements. In one example, the electronic device 1202 may be mounted next to a user model 1225 (e.g., HATS) or held next to a user 1225. The electronic device 1202 may then perform a calibration cycle for each calibration placement. For instance, calibration cycles may be performed for various positions, holding forces and/or couplings between the user model 1225 and the electronic device 1202, etc. In one approach, a user, technician and/or device repeatedly adjusts the calibration placement of the electronic device 1202 and the electronic device 1202 determines 1302 to perform calibration cycles (e.g., the electronic device 1202 receives a button press from a user or technician indicating that a calibration cycle should be performed, the electronic device 1202 senses that the calibration placement has changed and is stable, the electronic device 1202 receives a signal from an automated calibration device, etc.). In this way, several calibration parameters 1211 or sets of calibration parameters 1211 may be determined by the electronic device 1202. If the electronic device 1202 determines 1302 not to perform a calibration cycle (e.g., calibration has ended, a threshold number of calibration parameters 1211 have been determined, the electronic device 1202 is entering runtime, etc.), electronic device 1202 operation may proceed to runtime operations.

If the electronic device 1202 determines 1302 to perform a calibration cycle, the electronic device 1202 may determine 1304 at least one calibration active noise control parameter. Examples of active noise control parameters include filter coefficients, transfer functions, filter taps and/or one or more filter characteristics (e.g., frequency response, magnitude response, phase response, etc.). In some implementations, in a calibration cycle, the electronic device 1202 may be mounted on the user model 1225. For example, the actual transfer function or channel response between the speaker 1220 and the ear may be measured using the electronic device 1202 and/or the user model 1225. The measured transfer function or channel response may be utilized to determine 1304 the calibration active noise control parameter(s) directly. As further described below and at approximately the same time, for example, a calibration ultrasound channel signal may be utilized to determine 1310 at least one calibration channel response parameter. The association between the calibration active noise control parameter and the calibration channel response may be established and stored in memory, for instance.

The electronic device 1202 may output 1306 a calibration ultrasound signal. For example, the ultrasound signal generator 1213 may provide an electronic ultrasound signal to the speaker 1220, which may output the calibration ultrasound signal.

The electronic device 1202 may receive 1308 a calibration ultrasound channel signal. For example, the acoustic channel signal 1227 may include an acoustic calibration ultrasound channel signal, which may be captured by the error microphone 1229, converted to an electronic calibration ultrasound channel signal and provided to the noise control circuitry 1209. Additionally or alternatively, the calibration ultrasound channel signal may be received by a separate microphone (e.g., an ear simulation microphone) mounted in the user model 1225. In some cases, the separate microphone may be coupled to the electronic device 1202 via a microphone jack. Additionally or alternatively, the separate microphone may be coupled to another device, in which case the calibration ultrasound channel signal may be recorded by the other device and transmitted to the electronic device 1202, which may receive 1308 the calibration ultrasound channel signal.

The electronic device 1202 may determine 1310 at least one calibration channel response parameter based on the calibration ultrasound channel signal. For example, the channel response determination block/module 1215 may determine calibration channel response statistics based on the calibration ultrasound channel signal. For example, in a calibration cycle, the electronic device 1202 may be mounted on the user model 1225. In some implementations, the actual transfer function or channel response between the speaker 1220 and the ear may be measured using the electronic device 1202 and/or the user model 1225. For example, the electronic device 102 may play a sine tone or white noise (e.g., the calibration ultrasound signal) through the electronic device 1202 speaker 1220. The generated sound may be recorded using the error microphone 1229 or through the user model's 1225 ear simulation microphone as described above. By applying standard identification techniques, the transfer function between the played signal and the recorded signal may be calculated. The calculated transfer function may be the same as the channel response. In particular, for the ultrasound channel response, a sine tone sweep in the ultrasound range or band limited white noise in the ultrasound range may be used as the calibration ultrasound channel signal. A transfer function between the output and received signal for the ultrasound range may be estimated via some system identification technique or by correlating the received 1308 signal calibration ultrasound channel signal to the output 1306 calibration ultrasound signal.

In some configurations, one or more of the calibration parameters 1211 (e.g., calibration channel response parameter(s) and/or active noise control parameter(s)) may be stored for use during runtime. As described above, one or more of the calibration procedures described in connection with the method 1300 may be repeated for various calibration placements. For example, each calibration parameter 1211 or set of calibration parameters 1211 determined may correspond to a particular calibration placement of the electronic device 1202.

Figure 14:
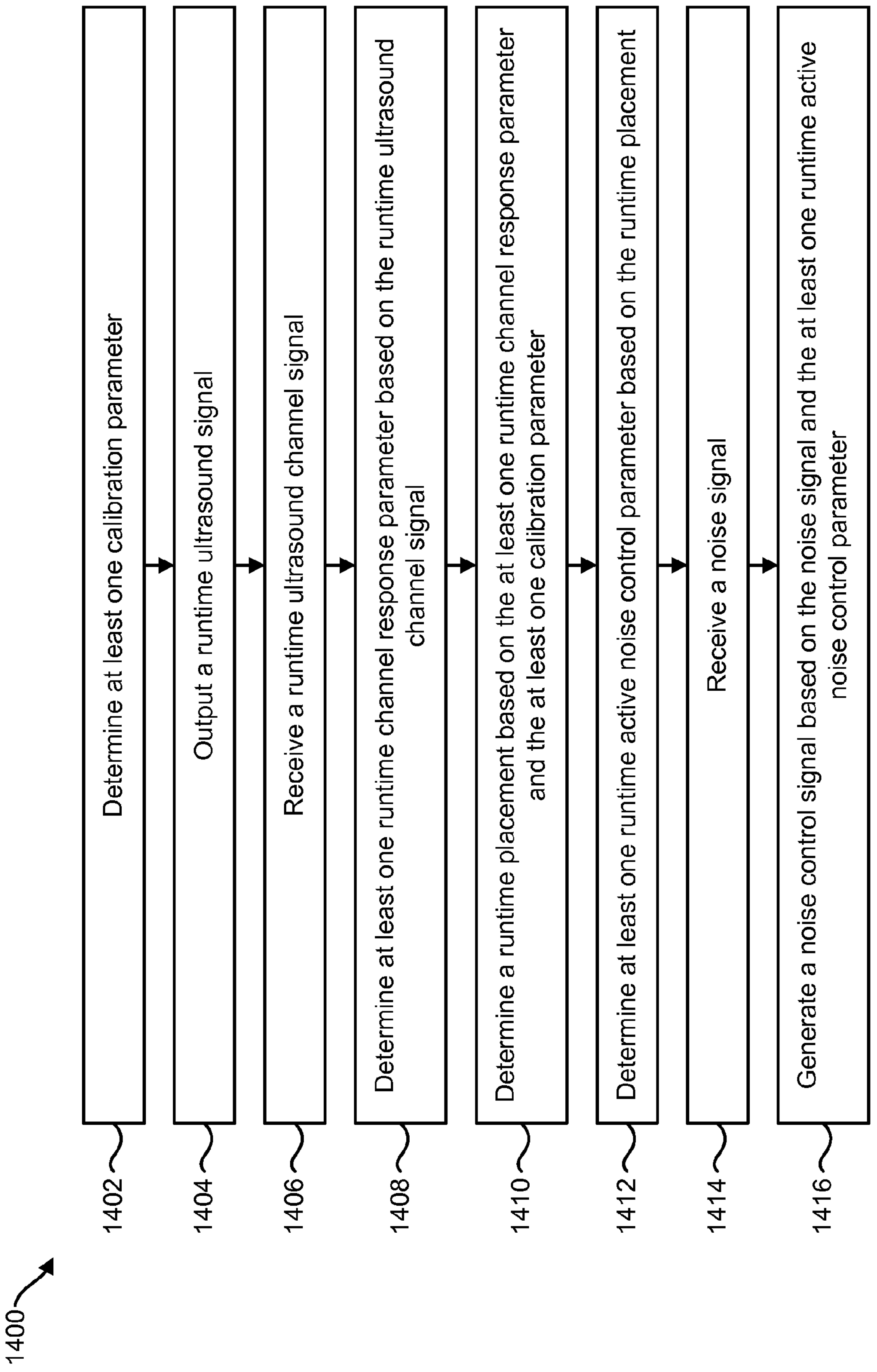
FIG. 14 is a flow diagram illustrating one configuration of a method for controlling noise by an electronic device.

FIG. 14 is a flow diagram illustrating one configuration of a method 1400 for controlling noise by an electronic device 1202. The electronic device 1202 may determine 1402 at least one calibration parameter 1211. For example, the electronic device 1202 may perform the method 1300 described in connection with FIG. 13 to determine 1402 at least one calibration parameter 1211. During runtime (when the electronic device 1202 is in use, for example), the electronic device 1202 may output 1404 a runtime ultrasound signal. For example, the ultrasound signal generator 1213 may provide an electronic ultrasound signal to the speaker 1220, which may output the runtime ultrasound signal.

The electronic device 1202 may receive 1406 a runtime ultrasound channel signal. For example, the acoustic channel signal 1227 may include an acoustic runtime ultrasound channel signal, which may be received by the error microphone 1229, converted to an electronic runtime ultrasound channel signal and provided to the noise control circuitry 1209.

The electronic device 1202 may determine 1408 at least one runtime channel response parameter based on the runtime ultrasound channel signal. For example, the channel response determination block/module 1215 may determine runtime channel response statistics based on the runtime ultrasound channel signal.

The electronic device 1202 may determine 1410 a runtime placement based on the at least one runtime channel response parameter and the at least one calibration parameter. For example, the placement determination block/module 1217 may determine 1410 a runtime placement by selecting a calibration placement with at least one calibration channel response parameter that is similar to (e.g., most similar to, numerically nearest to, etc.) the at least one runtime channel response parameter. Additionally or alternatively, the placement determination block/module 1217 may determine a runtime placement by selecting multiple calibration placements with a range of calibration channel response parameters. For instance, the placement determination block/module 1217 may select calibration placements with calibration channel response statistics neighboring the runtime channel response statistics (e.g., that are nearest to, greater than and/or less than the runtime channel response statistics). Thus, the electronic device 1202 may deduce a runtime placement that is similar to a calibration placement corresponding to one or more calibration parameters.

The electronic device 1202 may determine 1412 at least one runtime active noise control parameter based on the runtime placement. In one example, the runtime placement may correspond to a selected calibration placement with calibration channel response parameters similar to the runtime channel response parameters. In this example, the runtime active noise control parameter(s) may be selected from calibration active noise control parameter(s) corresponding to the selected calibration placement. In another example, the one or more runtime active noise control parameter(s) may be interpolated from calibration active noise control parameters corresponding to calibration placements with calibration channel response parameters neighboring the runtime channel response parameters (that correspond to the runtime placement).

The electronic device 1202 may receive 1414 a noise signal 1206. For example, the noise microphone 1204 may capture an acoustic noise signal 1222 and convert it to an electrical or electronic noise signal 1206 that may be provided to the noise control circuitry 1209.

The electronic device 1202 may generate 1416 a noise control signal based on the noise signal 1206 and the runtime active noise control parameter(s). For example, the noise control signal may be used to reduce or cancel the acoustic noise 1222. For instance, the noise control signal (which may be part or all of the signal 1221, for example) may be provided to a speaker 1220 that converts the noise control signal into an acoustic noise control signal (which may be part or all of the acoustic signal 1223, for example). In some configurations, the noise control signal may be generated 1416 by applying the runtime active noise control parameter(s) to a filter that filters the noise signal 1206.

Figure 15:
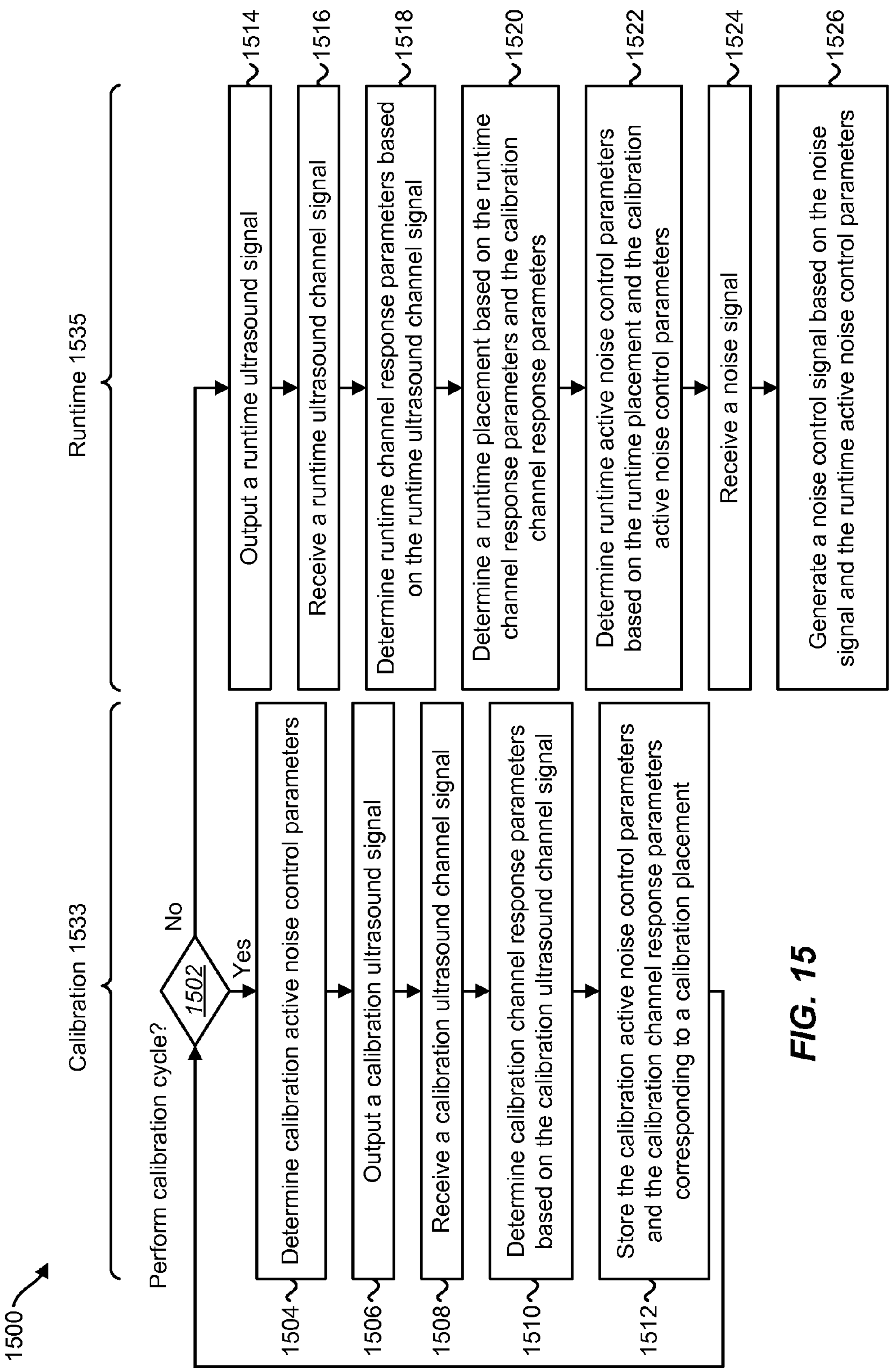
FIG. 15 is a flow diagram illustrating a more specific configuration of a method for controlling noise by an electronic device.

FIG. 15 is a flow diagram illustrating a more specific configuration of a method 1500 for controlling noise by an electronic device 1202. In particular, several calibration 1533 procedures and several runtime 1535 procedures are illustrated in FIG. 15. The electronic device 1202 may determine 1502 whether to perform a calibration cycle. In some configurations, the electronic device 1202 determines 1502 whether to perform a calibration cycle based on a one or more factors as described above in connection with FIG. 13. In one example, a calibration cycle may include determining 1504 calibration active noise control parameters, outputting 1506 a calibration ultrasound signal, receiving 1508 a calibration ultrasound channel signal, determining 1510 calibration channel response parameters based on the calibration ultrasound channel signal and storing 1512 the calibration active noise control parameters and the calibration channel response parameters corresponding to a calibration placement.

Determining 1502 whether to perform a calibration cycle may enable the electronic device 1202 to perform calibration cycles for multiple different calibration placements. In one example, the electronic device 1202 may be mounted next to a user model 1225 (e.g., HATS) or held next to a user 1225. The electronic device 1202 may then perform a calibration cycle for each calibration placement. For instance, calibration cycles may be performed for various positions, holding forces and/or couplings between the user model 1225 and the electronic device 1202, etc. In one approach, a user, technician and/or device repeatedly adjusts the calibration placement of the electronic device 1202 and the electronic device 1202 determines 1502 to perform calibration cycles (e.g., the electronic device 1202 receives a button press from a user or technician indicating that a calibration cycle should be performed, the electronic device 1202 senses that the calibration placement has changed and is stable, the electronic device 1202 receives a signal from an automated calibration device, etc.). In this way, several calibration parameters 1211 or sets of calibration parameters 1211 may be determined by the electronic device 1202. If the electronic device 1202 determines 1502 not to perform a calibration cycle (e.g., calibration has ended, a threshold number of calibration parameters 1211 have been determined, the electronic device 1202 is entering runtime 1535, etc.), electronic device 1202 operation may proceed to runtime 1535 operations.

If the electronic device 1202 determines 1502 to perform a calibration cycle, the electronic device 1202 may determine 1504 calibration active noise control parameters. Examples of active noise control parameters include filter coefficients, transfer functions, filter taps and/or one or more filter characteristics (e.g., frequency response, magnitude response, phase response, etc.).

The electronic device 1202 may output 1506 a calibration ultrasound signal. For example, the ultrasound signal generator 1213 may provide an electronic ultrasound signal to the speaker 1220, which may output the calibration ultrasound signal.

The electronic device 1202 may receive 1508 a calibration ultrasound channel signal. For example, the acoustic channel signal 1227 may include an acoustic calibration ultrasound channel signal, which may be captured by the error microphone 1229, converted to an electronic calibration ultrasound channel signal and provided to the noise control circuitry 1209.

The electronic device 1202 may determine 1510 calibration channel response parameters based on the calibration ultrasound channel signal. For example, the channel response determination block/module 1215 may determine calibration channel response statistics based on the calibration ultrasound channel signal.

The electronic device 1202 may store 1512 the calibration active noise control parameters and the calibration channel response parameters corresponding to a calibration placement. For example, the calibration active noise control parameters and the calibration channel response parameters corresponding to a calibration placement may be stored in memory, in registers, in a lookup table, in a database, etc. One or more of the calibration 1533 procedures described in connection with the method 1500 may be repeated for various calibration placements. For example, each calibration parameter 1211 or set of calibration parameters 1211 determined may correspond to a particular calibration placement of the electronic device 1202.

If the electronic device 1202 determines 1502 not to perform a calibration cycle, the electronic device 1202 may proceed to perform runtime 1535 operations. This may occur, for example, if a threshold number of calibration cycles have been performed for a variety for calibration placements, if the electronic device 1202 is in use and/or if a received input indicates that calibration is ended. In one example, runtime 1535 operations may include outputting 1514 a runtime ultrasound signal, receiving 1516 a runtime ultrasound channel signal, determining 1518 runtime channel response parameters based on the runtime ultrasound channel signal, determining 1520 a runtime placement based on the runtime channel response parameters and the calibration channel response parameters, determining 1522 runtime active noise control parameters based on the runtime placement and the calibration active noise control parameters, receiving 1524 a noise signal and generating 1526 a noise control signal based on the noise signal and the runtime active noise control parameters.

The electronic device 1202 may output 1514 a runtime ultrasound signal. For example, the ultrasound signal generator 1213 may provide an electronic ultrasound signal to the speaker 1220, which may output the runtime ultrasound signal.

The electronic device 1202 may receive 1516 a runtime ultrasound channel signal. For example, the acoustic channel signal 1227 may include an acoustic runtime ultrasound channel signal, which may be received by the error microphone 1229, converted to an electronic runtime ultrasound channel signal and provided to the noise control circuitry 1209.

The electronic device 1202 may determine 1518 runtime channel response parameters based on the runtime ultrasound channel signal. For example, the channel response determination block/module 1215 may determine runtime channel response statistics based on the runtime ultrasound channel signal.

The electronic device 1202 may determine 1520 a runtime placement based on the runtime channel response parameters and the calibration channel response parameters. For example, the placement determination block/module 1217 may determine 1520 a runtime placement by selecting a calibration placement with calibration channel response parameters that are similar to (e.g., most similar to) the runtime channel response parameters. Additionally or alternatively, the placement determination block/module 1217 may determine a runtime placement by selecting multiple calibration placements with a range of calibration channel response parameters that includes the runtime channel response parameters. For instance, the placement determination block/module 1217 may select calibration placements with calibration channel response statistics neighboring the runtime channel response statistics (e.g., that are nearest to, greater than and less than the runtime channel response statistics). Thus, the electronic device 1202 may deduce a runtime placement that is similar to a calibration placement corresponding to one or more calibration parameters.

The electronic device 1202 may determine 1522 runtime active noise control parameters based on the runtime placement and the calibration active noise control parameters. In one example, the runtime placement may correspond to a selected calibration placement with calibration channel response parameters similar to the runtime channel response parameters. In this example, the runtime active noise control parameters may be selected from calibration active noise control parameters corresponding to the selected calibration placement. In another example, the one or more runtime active noise control parameters may be interpolated from calibration active noise control parameters corresponding to calibration placements with calibration channel response parameters neighboring the runtime channel response parameters (that corresponds to the runtime placement).

The electronic device 1202 may receive 1524 a noise signal 1206. For example, the noise microphone 1204 may capture an acoustic noise signal 1222 and convert it to an electrical or electronic noise signal 1206 that may be provided to the noise control circuitry 1209.

The electronic device 1202 may generate 1526 a noise control signal based on the noise signal 1206 and the runtime active noise control parameters. For example, the noise control signal may be used to reduce or cancel the acoustic noise 1222. For instance, the noise control signal (which may be part or all of the signal 1221, for example) may be provided to a speaker 1220 that converts the noise control signal into an acoustic noise control signal (which may be part or all of the acoustic signal 1223, for example). In some configurations, the noise control signal may be generated 1526 by applying the runtime active noise control parameter(s) to a filter that filters the noise signal 1206.

Figure 16:
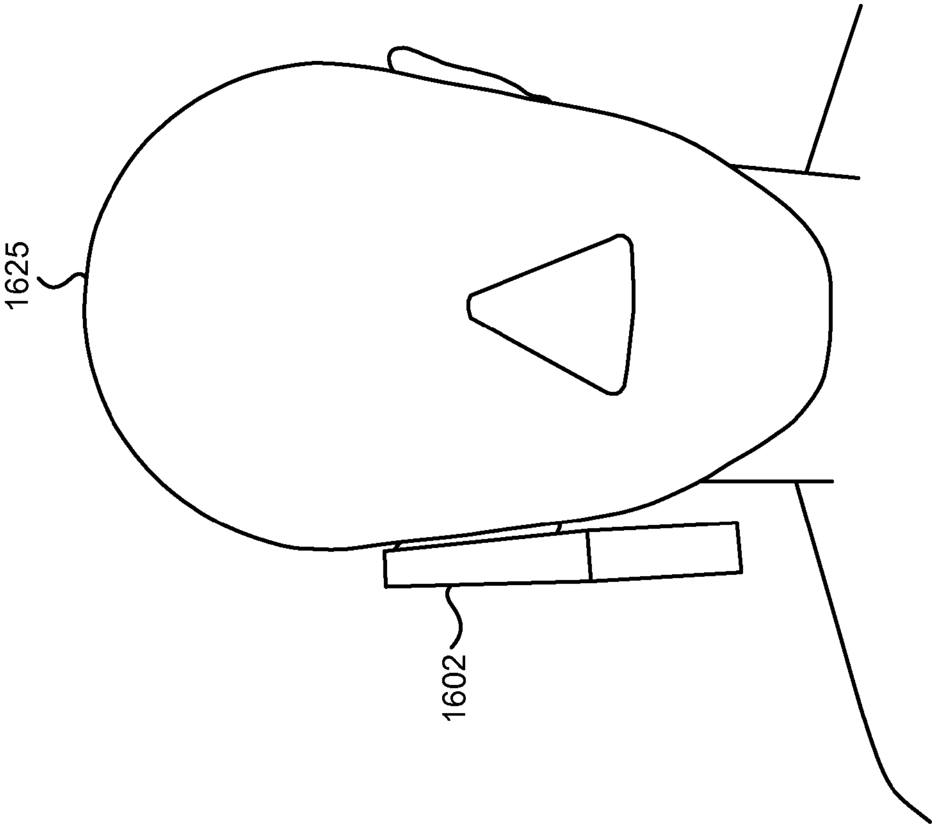
FIG. 16 is a diagram illustrating one example of a user or user model and an electronic device.

FIG. 16 is a diagram illustrating one example of a user 1625 or user model 1625 and an electronic device 1602. In particular, FIG. 16 illustrates a placement of the electronic device 1602 in relation to a user 1625 or user model 1625 (e.g., HATS). A placement may be or may depend on one or more of holding force, position, location, orientation, pressing force between the electronic device 1602 and a user 1625 or user model 1625 (e.g., HATS) and coupling (e.g., sealing) between the electronic device 1602 and a user 1625 or user model 1625 (e.g., HATS).

In one configuration, the electronic device 1602 may be mounted next to a user model 1625 (e.g., HATS) during calibration (e.g., measurement). The placement of the electronic device 1602 may be adjusted or varied between calibration cycles. For example, the electronic device 1602 may be mounted in a first placement with a particular orientation, position, holding force, pressing force and coupling for a first calibration cycle. Then, the placement of the electronic device 1602 may be adjusted to a second placement for a second calibration cycle. For instance, the holding force may be increased from 0 N to 4 N. This procedure may be repeated several times with different placements (e.g., different holding forces, positions, locations, orientations, pressing forces, and/or couplings (with differing leakages, for example)). In this way, the electronic device 1602 may determine and store multiple calibration parameters (e.g., calibration parameter sets) respectively corresponding to multiple calibration placements.

During runtime, a user 1625 may hold the electronic device 1602 next to his/her ear. For example, a user 1625 may press the electronic device 1602 against his/her ear. Alternatively, an electronic device 1602 may be mounted to the user 1625. For example, the electronic device 1602 may be a Bluetooth headset attached to the user's 1625 ear or may be a headset (e.g., pair of headphones) placed on the user's 1625 head. The electronic device 1602 placement may vary between uses and/or during use. For example, some users 1625 tend to press a cellular phone to their ear with greater force in a noisy environment. In some configurations of the systems and methods disclosed herein, the variation in the channel response between the electronic device 1602 and the user 1625 may be determined based on an ultrasound signal that is output from the electronic device 1602. For example, an ultrasound signal may be output from the earpiece of the electronic device 1602. An ultrasound channel signal may then be received (e.g., captured) by an error microphone near the earpiece and utilized to determine a runtime channel response. Runtime noise control parameters may then be determined and/or adjusted based on the runtime channel response. Accordingly, the systems and methods disclosed herein may improve active noise control performance.

Figure 17:
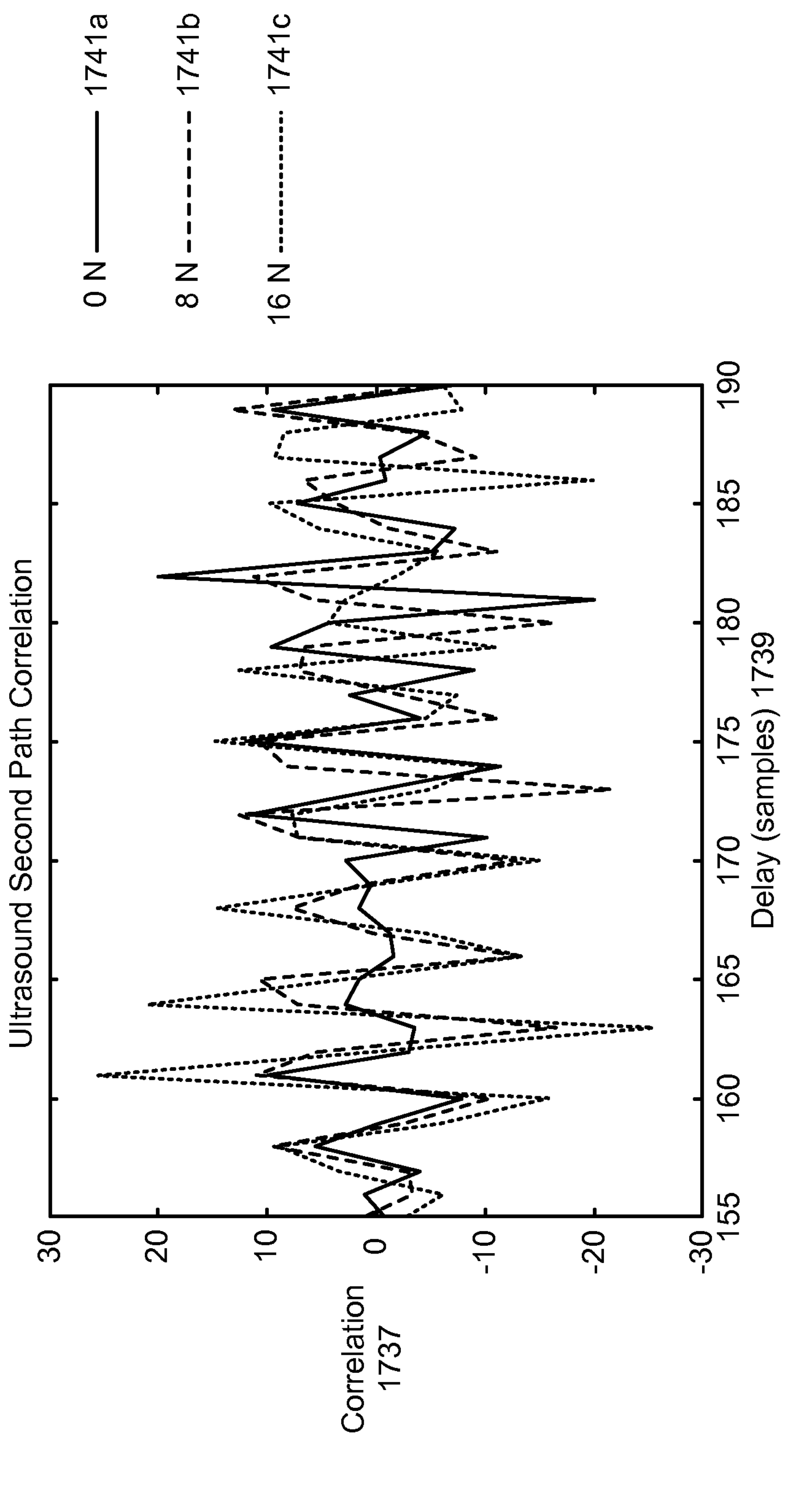
FIG. 17 is a graph illustrating ultrasound second path correlation with several holding forces.

FIG. 17 is a graph illustrating ultrasound second path correlation with several holding forces 1741*a-c*. In particular, FIG. 17 illustrates one example of ultrasound earpiece to error microphone correlation for various forces (in newtons (N)). The ultrasound second path may be similar to an active noise cancellation secondary path, but in the ultrasound frequency range (instead of in the audio frequency range, for example). For example, the ultrasound second path may signify the transfer function between the electronic device 1202 speaker 1220 and the error microphone 1229 (which may be located by the speaker 1220). FIG. 17 illustrates correlations of a received ultrasound signal (e.g., calibration ultrasound channel signal) versus an output ultrasound signal (e.g., calibration ultrasound signal). The horizontal axis in the graph illustrated in FIG. 17 shows a range of delay 1739 in samples at 96,000 samples/second (e.g., 96 kilohertz (kHz)). The vertical axis in the graph illustrated in FIG. 17 shows a range of correlation 1737. In particular, the graph in FIG. 17 includes plots of correlations between an ultrasound second path and a 0 N holding force 1741*a*, an 8 N holding force 1741*b* and a 16 N holding force 1741*c* over a range of delay 1739. As can be observed from the graph illustrated in FIG. 17, the holding force correlates with the ultrasound second path. For example, the correlation values may be proportional to the holding force. This correlation enables a placement (e.g., holding force) to be determined (e.g., estimated) based on an ultrasound channel signal as described above. For example, this is further illustrated in FIG. 18 as described below. In particular, when the holding force changes, the correlation coefficient may change with it.

Figure 18:
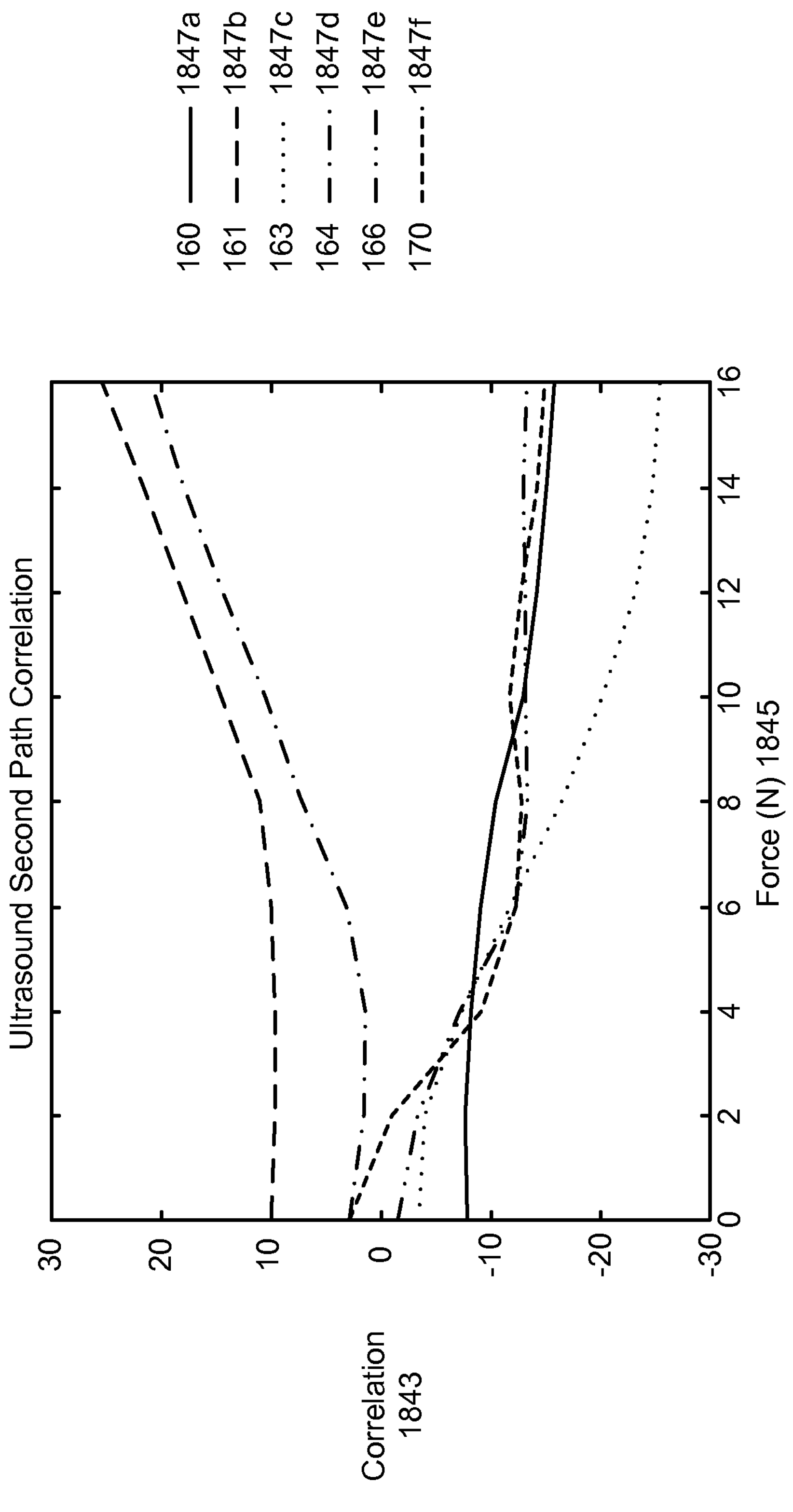
FIG. 18 is a graph illustrating ultrasound second path correlation with several coefficients.

FIG. 18 is a graph illustrating ultrasound second path correlation with several coefficients 1847*a-f*. The coefficients 1847*a-f* illustrated are selected correlation coefficients that co-vary with the holding force better than other correlation coefficients. In other words, the values of the selected correlation coefficients 1847*a-f* may be utilized to infer the holding force with a higher accuracy then other correlation coefficients, for example.

Some of the coefficients 1847*a-f* are illustrated in FIG. 17. For example, each line illustrates coefficients at a specific pressure level. The horizontal axis of FIG. 17 corresponds to a delay parameter of the coefficients 1847*a-f*. The vertical axis of FIG. 17 corresponds to the coefficient values. Thus, a line in FIG. 18 corresponds to coefficient values 1847*a-f* with a selected delay parameter. Accordingly, the coefficients 1847*a-f* illustrate that delay parameters in the range approximately between 160 and 170 may be utilized for each line. FIG. 18 illustrates that a coefficient with a specific delay parameter (e.g., especially 160 and 161) provides a near linear relationship to the applied pressure level.

The horizontal axis in the graph illustrated in FIG. 18 shows a range of holding force 1845 in newtons (N). The vertical axis in the graph illustrated in FIG. 18 shows a range of correlation 1843. In particular, the graph in FIG. 18 includes plots of several (e.g., selected) coefficients 1847*a-f* between an ultrasound output and received signal and over a range of force 1845. As can be observed from the graph illustrated in FIG. 18, the holding force correlates with the ultrasound second path. For example, the correlation values may be proportional to the holding force. This correlation enables a placement (e.g., holding force) to be determined (e.g., estimated) based on an ultrasound channel signal as described above.

Figure 19:
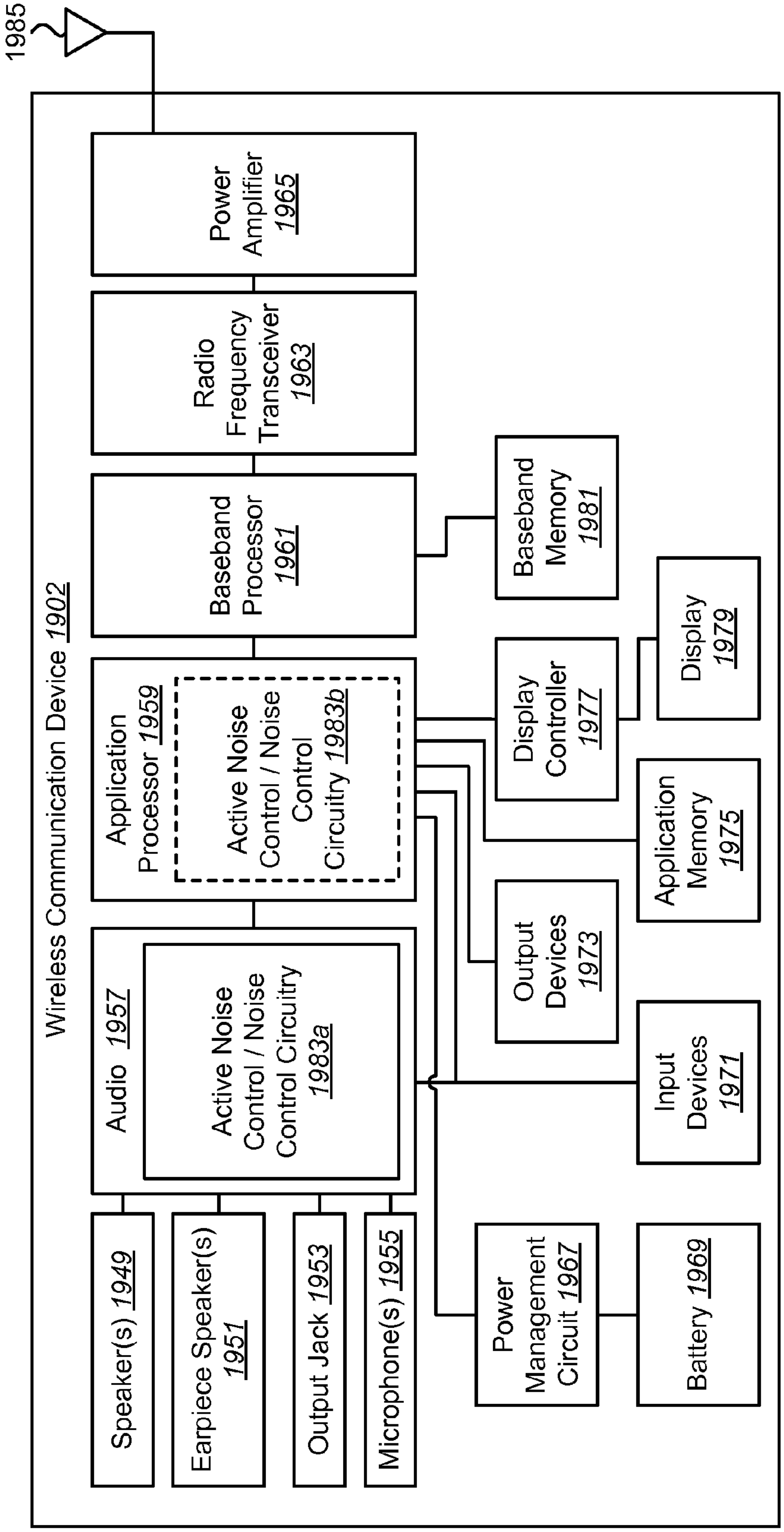
FIG. 19 is a block diagram illustrating one configuration of several components in a wireless communication device in which systems and methods for controlling noise may be implemented.

FIG. 19 is a block diagram illustrating one configuration of several components in a wireless communication device 1902 in which systems and methods for controlling noise may be implemented. Examples of wireless communication devices 1902 include cellular phones, smartphones, laptop computers, personal digital assistants (PDAs), digital music players, digital cameras, digital camcorders, game consoles, etc. The wireless communication device 1902 may be capable of communicating wirelessly with one or more other devices. The wireless communication device 1902 may include an application processor 1959. The application processor 1959 generally processes instructions (e.g., runs programs) to perform functions on the wireless communication device 1902. The application processor 1959 may be coupled to an audio block/module 1957.

The audio block/module 1957 may be an electronic device (e.g., integrated circuit) used for processing audio signals. For example, the audio block/module 1957 may include an audio codec for coding and/or decoding audio signals. The audio block/module 1957 may be coupled to one or more speakers 1949, one or more earpiece speakers 1951, an output jack 1953 and/or one or more microphones 1955. The speakers 1949 may include one or more electro-acoustic transducers that convert electrical or electronic signals into acoustic signals. For example, the speakers 1949 may be used to play music or output a speakerphone conversation, etc. The one or more earpiece speakers 1951 may include one or more speakers or electro-acoustic transducers that can be used to output acoustic signals (e.g., speech signals, ultrasonic signals, noise control signals, etc.) to a user. For example, one or more earpiece speakers 1951 may be used such that only a user may reliably hear an acoustic signal generated by the earpiece speakers 1951. The output jack 1953 may be used for coupling other devices to the wireless communication device 1902 for outputting audio, such as headphones. The speakers 1949, one or more earpiece speakers 1951 and/or the output jack 1953 may generally be used for outputting an audio signal from the audio block/module 1957. The one or more microphones 1955 may be acousto-electric transducers that convert an acoustic signal (such as a user's voice) into electrical or electronic signals that are provided to the audio block/module 1957.

An active noise control block/module and/or noise control circuitry 1983*a* may be optionally implemented as part of the audio block/module 1957. For example, the active noise control block/module and/or noise control circuitry 1983*a* may be implemented in accordance with one or more of the active noise control blocks/modules 108, 508 and noise control circuitry 1209 described above. For example, the active noise control block/module and/or noise control circuitry 1983*a* may receive a noise signal from one or more microphones 1955 or input device(s) 1971 (e.g., a port coupled to a remote microphone), may receive a force signal from the one or more input devices 1971 and/or may output a noise control signal using one or more earpiece speakers 1951, one or more speakers 1949 and/or the output jack

1953. Additionally or alternatively, the active noise control block/module and/or noise control circuitry 1983*a* may determine active noise control parameter(s), output ultrasound signals via the speaker(s) 1949 and/or earpiece speaker(s) 1951, receive ultrasound channel signals via the microphone(s) 1955, determine channel response parameter(s), determine placement(s), receive a noise signal from microphone(s) 1955 or input device(s) 1971 and may generate a noise control signal (which may be provided to one or more earpiece speakers 1951 and/or one or more speakers 1949 and/or the output jack 1953).

Additionally or alternatively, an active noise control block/module and/or noise control circuitry 1983*b* may be implemented in the application processor 1959. For example, the active noise control block/module and/or noise control circuitry 1983*b* may be implemented in accordance with one or more of the active noise control blocks/modules 108, 508 and noise control circuitry 1209 described above. For example, the active noise control block/module and/or noise control circuitry 1983*b* may receive a noise signal from one or more microphones 1955 or input device(s) 1971, may receive a force signal from the one or more input devices 1971 and may output a noise control signal using one or more earpiece speakers 1951, one or more speakers 1949 and/or the output jack 1953. Additionally or alternatively, the active noise control block/module and/or noise control circuitry 1983*b* may determine active noise control parameter(s), output ultrasound signals via the speaker(s) 1949 and/or earpiece speaker(s) 1951, receive ultrasound channel signals via the microphone(s) 1955, determine channel response parameter(s), determine placement(s), receive a noise signal from microphone(s) 1955 or input device(s) 1971 and may generate a noise control signal (which may be provided to one or more earpiece speakers 1951 one or more speakers 1949 and/or the output jack 1953). In another configuration, an active noise control block/module may be implemented independently from the audio block/module 1957 and/or the application processor 1959.

The application processor 1959 may be coupled to a power management circuit 1967. One example of a power management circuit 1967 is a power management integrated circuit (PMIC), which may be used to manage the electrical power consumption of the wireless communication device 1902. The power management circuit 1967 may be coupled to a battery 1969. The battery 1969 may generally provide electrical power to the wireless communication device 1902. It should be noted that the power management circuit 1967 and/or the battery 1969 may be coupled to one or more of the elements (e.g., all) included in the wireless communication device 1902.

The application processor 1959 may be coupled to one or more input devices 1971 for receiving input. Examples of input devices 1971 include infrared sensors, image sensors, accelerometers, touch sensors, force (e.g., pressure) sensors, keypads, microphones, input ports/jacks, etc. The input devices 1971 may allow user interaction with the wireless communication device 1902. The application processor 1959 may also be coupled to one or more output devices 1973. Examples of output devices 1973 include printers, projectors, screens, haptic devices, speakers, etc. The output devices 1973 may allow the wireless communication device 1902 to produce an output that may be experienced by a user.

The application processor 1959 may be coupled to application memory 1975. The application memory 1975 may be any electronic device that is capable of storing electronic information. Examples of application memory 1975 include double data rate synchronous dynamic random access memory (DDRAM), synchronous dynamic random access memory (SDRAM), flash memory, etc. The application memory 1975 may provide storage for the application processor 1959. For instance, the application memory 1975 may store data and/or instructions for the functioning of programs that are run on the application processor 1959. In one configuration, the application memory 1975 may store and/or provide data and/or instructions for performing one or more of the methods 400, 700, 1300, 1400, 1500 described above.

The application processor 1959 may be coupled to a display controller 1977, which in turn may be coupled to a display 1979. The display controller 1977 may be a hardware block that is used to generate images on the display 1979. For example, the display controller 1977 may translate instructions and/or data from the application processor 1959 into images that can be presented on the display 1979. Examples of the display 1979 include liquid crystal display (LCD) panels, light emitting diode (LED) panels, cathode ray tube (CRT) displays, plasma displays, etc.

The application processor 1959 may be coupled to a baseband processor 1961. The baseband processor 1961 generally processes communication signals. For example, the baseband processor 1961 may demodulate and/or decode received signals. Additionally or alternatively, the baseband processor 1961 may encode and/or modulate signals in preparation for transmission.

The baseband processor 1961 may be coupled to baseband memory 1981. The baseband memory 1981 may be any electronic device capable of storing electronic information, such as SDRAM, DDRAM, flash memory, etc. The baseband processor 1961 may read information (e.g., instructions and/or data) from and/or write information to the baseband memory 1981. Additionally or alternatively, the baseband processor 1961 may use instructions and/or data stored in the baseband memory 1981 to perform communication operations.

The baseband processor 1961 may be coupled to a radio frequency (RF) transceiver 1963. The RF transceiver 1963 may be coupled to one or more power amplifiers 1965 and one or more antennas 1985. The RF transceiver 1963 may transmit and/or receive radio frequency signals. For example, the RF transceiver 1963 may transmit an RF signal using a power amplifier 1965 and one or more antennas 1985. The RF transceiver 1963 may also receive RF signals using the one or more antennas 1985.

Figure 20:
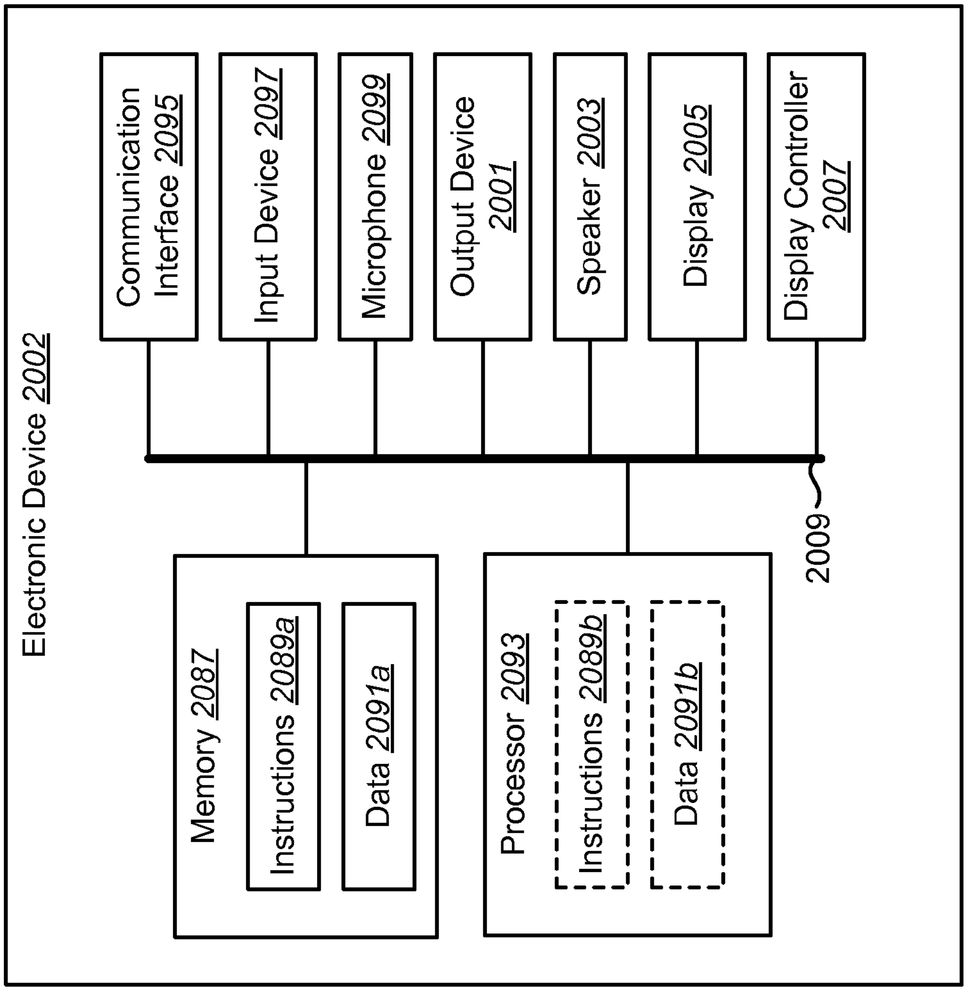
FIG. 20 illustrates various components that may be utilized in an electronic device.

FIG. 20 illustrates various components that may be utilized in an electronic device 2002. The illustrated components may be located within the same physical structure or in separate housings or structures. In some configurations, one or more of the electronic devices 102, 502, 1202, 1602, handsets 802, 902, 1002, 1102 and/or the wireless communication device 1902 described previously may be implemented in accordance with the electronic device 2002 illustrated in FIG. 20. The electronic device 2002 includes a processor 2093. The processor 2093 may be a general purpose single- or multi-chip microprocessor (e.g., an ARM), a special purpose microprocessor (e.g., a digital signal processor (DSP)), a microcontroller, a programmable gate array, etc. The processor 2093 may be referred to as a central processing unit (CPU). Although just a single processor 2093 is shown in the electronic device 2002 of FIG. 20, in an alternative configuration, a combination of processors 2093 (e.g., an ARM and DSP) could be used.

The electronic device 2002 also includes memory 2087 in electronic communication with the processor 2093. That is, the processor 2093 can read information from and/or write information to the memory 2087. The memory 2087 may be any electronic component capable of storing electronic information. The memory 2087 may be random access memory (RAM), read-only memory (ROM), magnetic disk storage media, optical storage media, flash memory devices in RAM, on-board memory included with the processor 2093, programmable read-only memory (PROM), erasable programmable read-only memory (EPROM), electrically erasable PROM (EEPROM), registers, and so forth, including combinations thereof.

Data 2091*a* and instructions 2089*a* may be stored in the memory 2087. The instructions 2089*a* may include one or more programs, routines, sub-routines, functions, procedures, etc. The instructions 2089*a* may include a single computer-readable statement or many computer-readable statements. The instructions 2089*a* may be executable by the processor 2093 to implement one or more of the methods 400, 700, 1300, 1400, 1500 described above. Executing the instructions 2089*a* may involve the use of the data 2091*a* that is stored in the memory 2087. FIG. 20 shows some instructions 2089*b* and data 2091*b* being loaded into the processor 2093 (which may originate from instructions 2089*a* and data 2091*a*).

The electronic device 2002 may also include one or more communication interfaces 2095 for communicating with other electronic devices. The communication interface 2095 may be based on wired communication technology, wireless communication technology, or both. Examples of different types of communication interfaces 2095 include a serial port, a parallel port, a Universal Serial Bus (USB), an Ethernet adapter, an IEEE 1394 bus interface, a small computer system interface (SCSI) bus interface, an infrared (IR) communication port, a Bluetooth wireless communication adapter, and so forth.

The electronic device 2002 may also include one or more input devices 2097 and one or more output devices 2001. Examples of different kinds of input devices 2097 include a keyboard, mouse, microphone, remote control device, button, joystick, trackball, touchpad, lightpen, etc. For instance, the electronic device 2002 may include one or more microphones 2099 for capturing acoustic signals. In one configuration, a microphone 2099 may be a transducer that converts acoustic signals (e.g., voice, speech, noise, etc.) into electrical or electronic signals. Examples of different kinds of output devices 2001 include a speaker, printer, etc. For instance, the electronic device 2002 may include one or more speakers 2003. In one configuration, a speaker 2003 may be a transducer that converts electrical or electronic signals into acoustic signals.

One specific type of output device 2001 which may be included in an electronic device 2002 is a display device 2005. Display devices 2005 used with configurations disclosed herein may utilize any suitable image projection technology, such as a cathode ray tube (CRT), liquid crystal display (LCD), light-emitting diode (LED), gas plasma, electroluminescence, or the like. A display controller 2007 may also be provided, for converting data 2091*a* stored in the memory 2087 into text, graphics, and/or moving images (as appropriate) shown on the display device 2005.

The various components of the electronic device 2002 may be coupled together by one or more buses, which may include a power bus, a control signal bus, a status signal bus, a data bus, etc. For simplicity, the various buses are illustrated in FIG. 20 as a bus system 2009. It should be noted that FIG. 20 illustrates only one possible configuration of an electronic device 2002. Various other architectures and components may be utilized.

Figure 21:
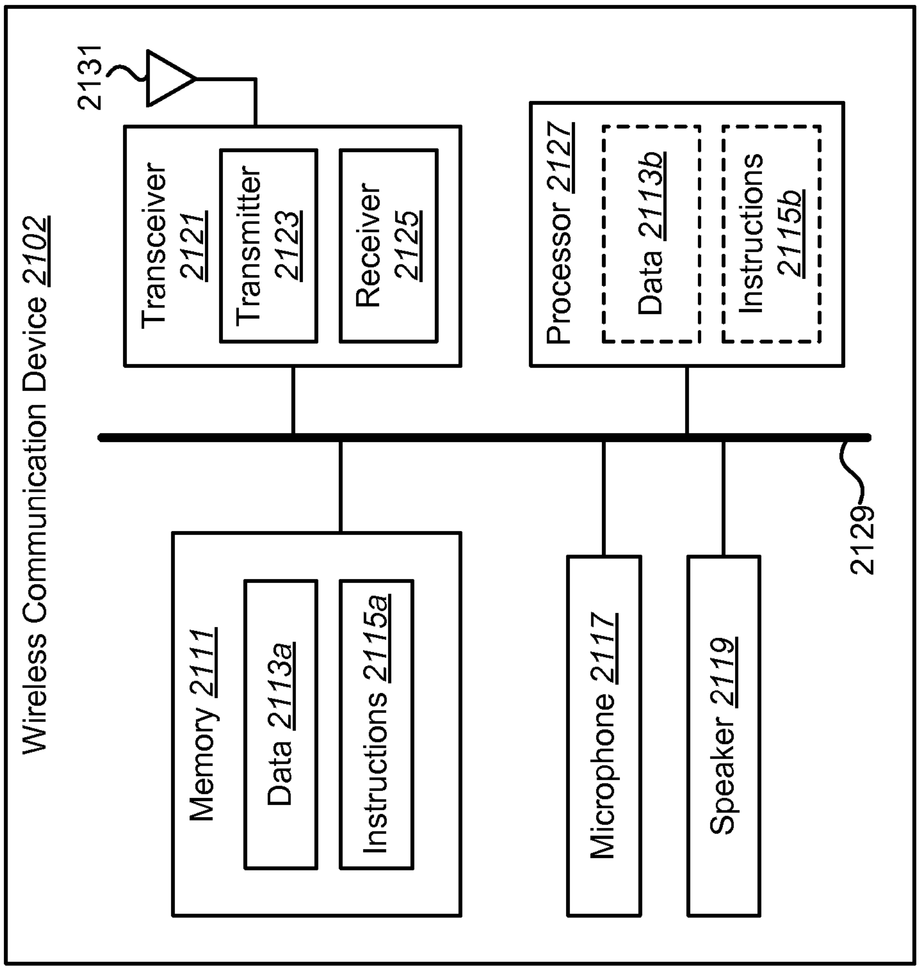
FIG. 21 illustrates certain components that may be included within a wireless communication device.

FIG. 21 illustrates certain components that may be included within a wireless communication device 2102. In some configurations, one or more of the electronic devices 102, 502, 1202, 1602, 2002, handsets 802, 902, 1002, 1102 and/or the wireless communication device 1902 described previously may be implemented in accordance with the wireless communication device 2102 illustrated in FIG. 21.

The wireless communication device 2102 includes a processor 2127. The processor 2127 may be a general purpose single- or multi-chip microprocessor (e.g., an ARM), a special purpose microprocessor (e.g., a digital signal processor (DSP)), a microcontroller, a programmable gate array, etc. The processor 2127 may be referred to as a central processing unit (CPU). Although just a single processor 2127 is shown in the wireless communication device 2102 of FIG. 21, in an alternative configuration, a combination of processors 2127 (e.g., an ARM and DSP) could be used.

The wireless communication device 2102 also includes memory 2111 in electronic communication with the processor 2127 (e.g., the processor 2127 can read information from and/or write information to the memory 2111). The memory 2111 may be any electronic component capable of storing electronic information. The memory 2111 may be random access memory (RAM), read-only memory (ROM), magnetic disk storage media, optical storage media, flash memory devices in RAM, on-board memory included with the processor 2127, programmable read-only memory (PROM), erasable programmable read-only memory (EPROM), electrically erasable PROM (EEPROM), registers, and so forth, including combinations thereof.

Data 2113*a* and instructions 2115*a* may be stored in the memory 2111. The instructions 2115*a* may include one or more programs, routines, sub-routines, functions, procedures, code, etc. The instructions 2115*a* may include a single computer-readable statement or many computer-readable statements. The instructions 2115*a* may be executable by the processor 2127 to implement one or more of the methods 400, 700, 1300, 1400, 1500 described above. Executing the instructions 2115*a* may involve the use of the data 2113*a* that is stored in the memory 2111. FIG. 21 shows some instructions 2115*b* and data 2113*b* being loaded into the processor 2127 (which may come from instructions 2115*a* and data 2113*a* in memory 2111).

The wireless communication device 2102 may also include a transmitter 2123 and a receiver 2125 to allow transmission and reception of signals between the wireless communication device 2102 and a remote location (e.g., another electronic device, wireless communication device, etc.). The transmitter 2123 and receiver 2125 may be collectively referred to as a transceiver 2121. An antenna 2131 may be electrically coupled to the transceiver 2121. The wireless communication device 2102 may also include (not shown) multiple transmitters 2123, multiple receivers 2125, multiple transceivers 2121 and/or multiple antenna 2131.

In some configurations, the wireless communication device 2102 may include one or more microphones 2117 for capturing acoustic signals. In one configuration, a microphone 2117 may be a transducer that converts acoustic signals (e.g., voice, speech, noise, etc.) into electrical or electronic signals. Additionally or alternatively, the wireless communication device 2102 may include one or more speakers 2119. In one configuration, a speaker 2119 may be a transducer that converts electrical or electronic signals into acoustic signals.

The various components of the wireless communication device 2102 may be coupled together by one or more buses, which may include a power bus, a control signal bus, a status signal bus, a data bus, etc. For simplicity, the various buses are illustrated in FIG. 21 as a bus system 2129.

In accordance with the systems and methods disclosed herein, a circuit, in an electronic device, may be adapted to detect a force on the electronic device. The same circuit, a different circuit or a second section of the same or different circuit may be adapted to generate a noise control signal based on a noise signal and the force. In addition, the same circuit, a different circuit or a third section of the same or different circuit may be adapted to adapt an adaptive filter based on the force.

In accordance with the systems and methods disclosed herein, a circuit, in an electronic device, may be adapted to output a runtime ultrasound signal. The same circuit, a different circuit or a second section of the same or different circuit may be adapted to receive a runtime ultrasound channel signal. The same circuit, a different circuit or a third section of the same circuit or different circuit may be adapted to determine at least one calibration parameter. The same circuit, a different circuit or a fourth section of the same circuit or different circuit may be adapted to determine a runtime channel response based on the runtime ultrasound channel signal. The same circuit, a different circuit or a fifth section of the same circuit or different circuit may be adapted to determine a runtime placement based on the runtime channel response and the at least one calibration parameter. The same circuit, a different circuit or a sixth section of the same or different circuit may be adapted to determine at least one runtime active noise control parameter based on the runtime placement.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer or processor. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL) or wireless technologies such as infrared, radio and microwave, then the coaxial cable, fiber optic cable, twisted pair, DSL or wireless technologies such as infrared, radio and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It is to be understood that the claims are not limited to the precise configuration and components illustrated above. Various modifications, changes and variations may be made in the arrangement, operation and details of the systems, methods, and apparatus described herein without departing from the scope of the claims.

What is claimed is:

1. An electronic device for controlling noise, comprising:

a force sensor configured to detect a pressing force between the electronic device and a user; and noise control circuitry configured to generate a noise control signal based on a noise signal and an adaptive filter that is adapted based on the force, wherein the noise control circuitry is configured to adapt the adaptive filter by scaling a first base transfer function with a first scaling function of the force and scaling a second base transfer function with a second scaling function of the force and wherein the first scaling function decreases in magnitude as the force increases, and the second scaling function increases in magnitude as the force increases.

2. The electronic device of claim 1, further comprising a microphone for capturing the noise signal.

3. The electronic device of claim 1, further comprising a speaker for outputting the noise control signal.

4. The electronic device of claim 1, wherein adapting the adaptive filter is based on a correlation between a transfer function and the force.

5. The electronic device of claim 1, wherein adapting the adaptive filter comprises:

determining a first scaling factor and a second scaling factor based on the force;

multiplying the first base transfer function by the first scaling factor to produce a first product;

multiplying the second base transfer function by the second scaling factor to produce a second product; and multiplying a negative of the first product by a reciprocal of the second product to produce filter coefficients; and controlling the adaptive filter using the filter coefficients to generate the noise control signal.

6. The electronic device of claim 1, wherein adapting the adaptive filter is performed according to an equation $$W(z) = \frac{-g(R)P_o(z)}{[h(R)S_o(z)]},$$

wherein $P_o$ (z) is the first base transfer function at a first force, g is the first scaling function of a force value R, z is a complex number, $S_o$ (z) is the second base transfer function at a second force, h is the second scaling function of the force value R and W(z) represents the adaptive filter.

7. The electronic device of claim 1, wherein the force sensor continually measures the force and provides a force signal based on the force.

8. The electronic device of claim 7, wherein the adaptive filter is continually adapted based on the force signal.

9. The electronic device of claim 1, wherein generating the noise control signal does not involve an iterative convergence process but involves a direct calculation.

10. The electronic device of claim 1, wherein the electronic device does not use an error microphone signal for generating the noise control signal.

11. The electronic device of claim 1, wherein the electronic device comprises a plurality of force sensors for detecting the force on the electronic device.

12. The electronic device of claim 11, wherein the plurality of force sensors are positioned proximate corners of the electronic device.

13. The electronic device of claim 11, wherein the plurality of force sensors are positioned proximate a speaker on the electronic device.

14. The electronic device of claim 1, wherein the force sensor is positioned behind a speaker on the electronic device.

15. The electronic device of claim 1, wherein the force sensor is a gasket-type force sensor.

16. The electronic device of claim 1, wherein the force is a force between the electronic device and a user's ear or face.

17. The electronic device of claim 1, wherein the electronic device is a wireless communication device.

18. A method for controlling noise by an electronic device, comprising:

detecting a pressing force between an electronic device and a user; and generating a noise control signal based on a noise signal and adapting an adaptive filter based on the force, wherein adapting the adaptive filter based on the force comprises scaling a first base transfer function with a first scaling function of the force and scaling a second base transfer function with a second scaling function of the force, and wherein the first scaling function decreases in magnitude as the force increases, and the second scaling function increases in magnitude as the force increases.

19. The method of claim 18, further comprising capturing the noise signal.

20. The method of claim 18, further comprising outputting the noise control signal.

21. The method of claim 18, wherein adapting the adaptive filter is based on a correlation between a transfer function and the force.

22. The method of claim 18, wherein adapting the adaptive filter comprises:

determining a first scaling factor and a second scaling factor based on the force;

multiplying the first base transfer function by the first scaling factor to produce a first product;

multiplying the second base transfer function by the second scaling factor to produce a second product; and multiplying a negative of the first product by a reciprocal of the second product to produce filter coefficients; and controlling the adaptive filter using the filter coefficients to generate the noise control signal.

23. The method of claim 18, wherein adapting the adaptive filter is performed according to an equation $$W(z) = \frac{-g(R)P_o(z)}{[h(R)S_o(z)]},$$

wherein $P_o$ (z) is the first base transfer function at a first force, g is the first scaling function of a force value R, z is a complex number, $S_o$ (z) is the second base transfer function at a second force, h is the second scaling function of the force value R and W(z) represents the adaptive filter.

24. The method of claim 18, wherein a force sensor continually measures the force and provides a force signal based on the force.

25. The method of claim 24, wherein the adaptive filter is continually adapted based on the force signal.

26. The method of claim 18, wherein generating the noise control signal does not involve an iterative convergence process but involves a direct calculation.

27. The method of claim 18, wherein the electronic device does not use an error microphone signal for generating the noise control signal.

28. The method of claim 18, wherein a plurality of force sensors are used for detecting the force on the electronic device.

29. The method of claim 28, wherein the plurality of force sensors are positioned proximate corners of the electronic device.

30. The method of claim 28, wherein the plurality of force sensors are positioned proximate a speaker on the electronic device.

31. The method of claim 18, wherein a force sensor is positioned behind a speaker on the electronic device for detecting the force.

32. The method of claim 18, wherein a gasket-type force sensor is used for detecting the force.

33. The method of claim 18, wherein the force is a force between the electronic device and a user's ear or face.

34. The method of claim 18, wherein the electronic device is a wireless communication device.

35. A computer-program product for controlling noise, comprising a non-transitory tangible computer-readable medium having instructions thereon, the instructions comprising:

code for causing an electronic device to detect a pressing force between the electronic device and a user; and code for causing the electronic device to generate a noise control signal based on a noise signal and an adaptive filter that is adapted based on the force, comprising code for causing the electronic device to adapt the adaptive filter by scaling a first base transfer function with a first scaling function of the force and scaling a second base transfer function with a second scaling function of the force and wherein the first scaling function decreases in magnitude as the force increases, and the second scaling function increases in magnitude as the force increases.

36. The computer-program product of claim 35, wherein the code for causing the electronic device to adapt the adaptive filter is based on a correlation between a transfer function and the force.

37. The computer-program product of claim 35, wherein an error microphone signal is not used for generating the noise control signal.

38. The computer-program product of claim 35, wherein the force is a force between the electronic device and a user's ear or face.

39. An apparatus for controlling noise, comprising:

means for detecting a pressing force between the apparatus and a user; and means for generating a noise control signal based on a noise signal and adapting an adaptive filter based on the force, wherein the means for generating the noise control signal is configured to adapt the adaptive filter by scaling a first base transfer function with a first scaling function of the force and scaling a second base transfer function with a second scaling function of the force, and wherein the first scaling function decreases in magnitude as the force increases, and the second scaling function increases in magnitude as the force increases.

40. The apparatus of claim 39, wherein adapting the adaptive filter is based on a correlation between a transfer function and the force.

41. The apparatus of claim 39, wherein an error microphone signal is not used for generating the noise control signal.

42. The apparatus of claim 39, wherein the force is a force between the apparatus and a user's ear or face.

* * * * *